(12) United States Patent
Voellmicke et al.

(10) Patent No.: US 7,175,336 B2
(45) Date of Patent: Feb. 13, 2007

(54) GRAFT DELIVERY SYSTEM

(75) Inventors: John C. Voellmicke, Providence, RI (US); Stephen W. Connolly, Sharon, MA (US); Sudhakar Kadiyala, South Easton, MA (US); Scott P. Bruder, Sudbury, MA (US); David Urbahns, Barrington, RI (US); Kazuna Tanaka, CosCob, CT (US); Jeffrey Kapec, Westport, CT (US); Yukiko Naoi, New York, NY (US)

(73) Assignee: Depuy Acromed, Inc., Raynham, MA (US)

( * ) Notice: Subject to any disclaimer, the term of this patent is extended or adjusted under 35 U.S.C. 154(b) by 1266 days.

(21) Appl. No.: 09/771,433

(22) Filed: Jan. 26, 2001

(65) Prior Publication Data

US 2004/0167617 A1    Aug. 26, 2004

(51) Int. Cl.
*B01F 3/10* (2006.01)
*B01F 15/02* (2006.01)
*A61M 39/00* (2006.01)

(52) U.S. Cl. ............ 366/160.4; 366/189; 602/82

(58) Field of Classification Search ......... 137/606, 137/602; 604/83, 82, 416; 366/160.4, 189, 366/190
See application file for complete search history.

(56) References Cited

U.S. PATENT DOCUMENTS

| | | | |
|---|---|---|---|
| 2,158,593 A | 5/1939 | Scrimgeor | |
| 3,179,107 A | 4/1965 | Clark | |
| 3,223,083 A | 12/1965 | Cobey | |
| 3,470,893 A * | 10/1969 | Nelson | 137/68.11 |
| 4,040,420 A | 8/1977 | Speer | |
| 4,048,995 A | 9/1977 | Mittleman | |
| 4,109,653 A | 8/1978 | Kozam et al. | |
| 4,150,673 A | 4/1979 | Watt | |
| 4,274,163 A | 6/1981 | Malcom et al. | |
| 4,359,049 A | 11/1982 | Redl et al. | |
| 4,362,567 A | 12/1982 | Schwarz et al. | |
| 4,405,249 A | 9/1983 | Scales | |
| 4,414,976 A | 11/1983 | Schwarz et al. | |
| 4,447,230 A * | 5/1984 | Gula et al. | 604/122 |
| 4,526,303 A | 7/1985 | Harrod | |
| 4,526,909 A | 7/1985 | Urist | |
| 4,539,716 A | 9/1985 | Bell | |
| 4,551,135 A | 11/1985 | Gorman et al. | |
| 4,593,685 A | 6/1986 | McKay et al. | |
| 4,608,199 A | 8/1986 | Caplan et al. | |
| 4,609,551 A | 9/1986 | Caplan et al. | |

(Continued)

FOREIGN PATENT DOCUMENTS

| | | |
|---|---|---|
| EP | 0 711 535 | 5/1996 |
| EP | 0 901 773 | 3/1999 |
| EP | 0 955 022 | 11/1999 |

(Continued)

OTHER PUBLICATIONS

Roy L., Tawes et al.; Autologous Fibrin Glue: The Last Step in Operative Hemostasis; The American Journal of Surgery; vol. 168; Aug. 1994, 3 pgs.
Mehmet C. Oz, MD et al.; Autologous Fibrin Glue From Intraoperatively Collected Platelet Rich Plasma; The Society of Thoracic Surgeons; 1992, 2 pgs.
PCT International Search Report, dated Aug. 16, 2002, for PCT Appln. No. PCT/US02/02275.

*Primary Examiner*—Tony G. Soohoo
(74) *Attorney, Agent, or Firm*—Thomas M. DiMauro

(57) ABSTRACT

The invention relates to a manifold for mixing biomedical fluids having superior stability and minimal susceptibility to clotting.

6 Claims, 28 Drawing Sheets

U.S. PATENT DOCUMENTS

Figure 6A:
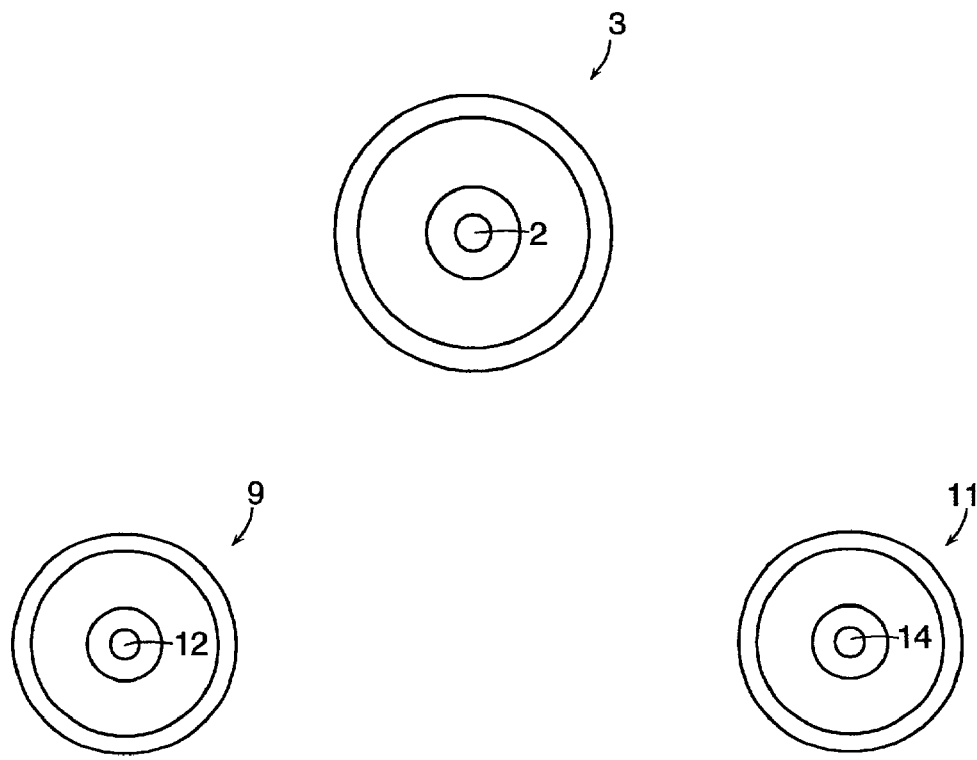

| | | | |
|---|---|---|---|
| 4,625,722 A | 12/1986 | Murray | |
| 4,627,434 A | 12/1986 | Murray | |
| 4,629,455 A | 12/1986 | Kanno | |
| 4,631,055 A | 12/1986 | Redl et al. | |
| 4,632,672 A | 12/1986 | Kvitrud | |
| 4,653,487 A | 3/1987 | Maale | |
| 4,714,457 A | 12/1987 | Alterbaum | |
| 4,735,616 A | 4/1988 | Eibl et al. | |
| 4,743,229 A | 5/1988 | Chu | |
| 4,751,921 A | 6/1988 | Park | |
| 4,769,011 A | 9/1988 | Swaniger | |
| 4,801,263 A | 1/1989 | Clark | |
| 4,820,306 A | 4/1989 | Gorman et al. | |
| 4,842,581 A | 6/1989 | Davis | |
| 4,871,088 A | 10/1989 | Cox | |
| 4,874,368 A | 10/1989 | Miller et al. | |
| 4,882,149 A | 11/1989 | Spector | |
| 4,915,688 A * | 4/1990 | Bischof et al. | 604/83 |
| 4,950,296 A | 8/1990 | McIntyre | |
| 4,978,336 A | 12/1990 | Capozzi et al. | |
| 4,979,942 A | 12/1990 | Wolf et al. | |
| 4,981,241 A | 1/1991 | Keller | |
| 4,994,065 A | 2/1991 | Gibbs et al. | |
| 5,010,009 A | 4/1991 | Steele et al. | |
| 5,030,215 A | 7/1991 | Morse et al. | |
| 5,049,135 A | 9/1991 | Davis | |
| 5,104,375 A | 4/1992 | Wolf et al. | |
| 5,110,604 A | 5/1992 | Chu et al. | |
| 5,112,354 A | 5/1992 | Sires | |
| 5,116,315 A | 5/1992 | Capozzi et al. | |
| 5,133,756 A | 7/1992 | Bauer et al. | |
| 5,152,763 A | 10/1992 | Johnson | |
| 5,181,918 A | 1/1993 | Brandhorst et al. | |
| 5,185,001 A | 2/1993 | Galanakis | |
| 5,190,524 A * | 3/1993 | Wex | 604/80 |
| 5,193,907 A | 3/1993 | Faccioli et al. | |
| 5,197,985 A | 3/1993 | Caplan et al. | |
| 5,226,877 A | 7/1993 | Epstein | |
| 5,226,914 A | 7/1993 | Caplan et al. | |
| 5,232,024 A | 8/1993 | Williams | |
| 5,286,258 A | 2/1994 | Haber et al. | |
| 5,290,259 A | 3/1994 | Fischer | |
| 5,314,412 A | 5/1994 | Rex | |
| 5,322,510 A | 6/1994 | Lindner et al. | |
| 5,368,563 A | 11/1994 | Lonneman et al. | |
| 5,376,079 A | 12/1994 | Holm | |
| 5,405,607 A | 4/1995 | Epstein | |
| 5,431,185 A * | 7/1995 | Shannon et al. | 137/512.4 |
| 5,435,645 A | 7/1995 | Faccioli et al. | |
| 5,443,531 A | 8/1995 | Ripamonti | |
| 5,454,792 A | 10/1995 | Tennican et al. | |
| 5,464,396 A | 11/1995 | Barta et al. | |
| 5,474,540 A | 12/1995 | Miller et al. | |
| 5,477,987 A | 12/1995 | Keller | |
| 5,478,323 A | 12/1995 | Westwood et al. | |
| 5,486,359 A | 1/1996 | Caplan et al. | |
| 5,520,658 A | 5/1996 | Holm | |
| 5,558,136 A | 9/1996 | Orrico | |
| 5,577,517 A | 11/1996 | Bonutti | |
| 5,605,255 A | 2/1997 | Reidel et al. | |
| 5,605,541 A | 2/1997 | Holm | |
| 5,645,729 A | 7/1997 | Priegnitz et al. | |
| 5,665,067 A | 9/1997 | Linder et al. | |
| 5,674,394 A * | 10/1997 | Whitmore | 210/321.8 |
| 5,694,951 A | 12/1997 | Bonutti | |
| 5,695,478 A * | 12/1997 | Haindl | 604/247 |
| 5,697,932 A | 12/1997 | Smith et al. | |
| 5,700,289 A | 12/1997 | Breitbart et al. | |
| 5,718,707 A | 2/1998 | Mikhail | |
| 5,718,899 A | 2/1998 | Gristina et al. | |
| 5,738,662 A * | 4/1998 | Shannon et al. | 604/247 |
| 5,759,171 A | 6/1998 | Coelho et al. | |
| 5,769,895 A | 6/1998 | Ripamonti | |
| 5,772,665 A | 6/1998 | Glad et al. | |
| 5,788,976 A | 8/1998 | Bradford | |
| 5,810,773 A * | 9/1998 | Pesnicak | 604/83 |
| 5,810,885 A | 9/1998 | Zinger | |
| 5,824,084 A | 10/1998 | Muschler | |
| 5,824,087 A | 10/1998 | Aspden et al. | |
| 5,910,315 A | 6/1999 | Stevenson et al. | |
| 5,925,051 A | 7/1999 | Mikhail | |
| 5,947,937 A | 9/1999 | Urrutia et al. | |
| 5,971,972 A | 10/1999 | Rosenbaum | |
| 5,975,367 A | 11/1999 | Coelho et al. | |
| 5,976,102 A | 11/1999 | Epstein | |
| 5,989,215 A | 11/1999 | Delmotte et al. | |
| 6,001,259 A | 12/1999 | Whitmore | |
| 6,007,515 A | 12/1999 | Epstein et al. | |
| 6,019,765 A | 2/2000 | Thornhill et al. | |
| 6,021,961 A | 2/2000 | Brown | |
| 6,045,555 A | 4/2000 | Smith et al. | |
| 6,047,861 A | 4/2000 | Vidal et al. | |
| 6,049,026 A | 4/2000 | Muschler | |
| 6,059,749 A | 5/2000 | Marx | |
| 6,063,055 A | 5/2000 | Epstein et al. | |
| 6,086,594 A | 7/2000 | Brown | |
| 6,116,773 A | 9/2000 | Murray | |
| 6,120,174 A | 9/2000 | Hoag et al. | |
| 6,132,396 A | 10/2000 | Antanavich et al. | |
| 6,136,030 A | 10/2000 | Lin et al. | |
| 6,139,509 A | 10/2000 | Yuan et al. | |
| 6,142,998 A | 11/2000 | Smith et al. | |
| 6,143,030 A | 11/2000 | Schroder | |
| 6,149,655 A | 11/2000 | Constantz et al. | |
| 6,160,033 A | 12/2000 | Nies | |
| 6,176,607 B1 | 1/2001 | Hajianpour | |
| 6,210,031 B1 | 4/2001 | Murray | |
| 6,214,012 B1 | 4/2001 | Karpman et al. | |
| 6,217,581 B1 | 4/2001 | Tolson | |
| 6,221,029 B1 | 4/2001 | Mathis et al. | |
| 6,238,399 B1 | 5/2001 | Heller et al. | |
| 6,254,268 B1 | 7/2001 | Long | |
| 6,264,660 B1 | 7/2001 | Schmidt et al. | |
| 6,273,916 B1 | 8/2001 | Murphy | |
| 6,293,971 B1 | 9/2001 | Nelson et al. | |
| 6,302,574 B1 | 10/2001 | Chan | |
| 6,309,395 B1 | 10/2001 | Smith et al. | |
| 6,309,420 B1 | 10/2001 | Preissman | |
| 6,312,149 B1 | 11/2001 | Sjovall et al. | |
| 6,348,055 B1 | 2/2002 | Preissman | |
| 6,626,468 B2 * | 9/2003 | Ogawa | 285/125.1 |
| 6,966,581 B2 * | 11/2005 | Mastropaolo | 285/93 |
| 2001/0016703 A1 | 8/2001 | Wironen et al. | |
| 2001/0037091 A1 | 11/2001 | Wironen et al. | |
| 2002/0010471 A1 | 1/2002 | Wironen et al. | |
| 2002/0010472 A1 | 1/2002 | Kuslich et al. | |
| 2002/0013553 A1 | 1/2002 | Pajunk et al. | |

FOREIGN PATENT DOCUMENTS

| | | |
|---|---|---|
| WO | WO 84/00340 A | 2/1984 |
| WO | WO 95/20408 A | 8/1995 |
| WO | 96/28117 | 9/1996 |
| WO | 98/16267 | 4/1998 |
| WO | 99/13805 | 3/1999 |
| WO | 00/45870 | 8/2000 |

* cited by examiner

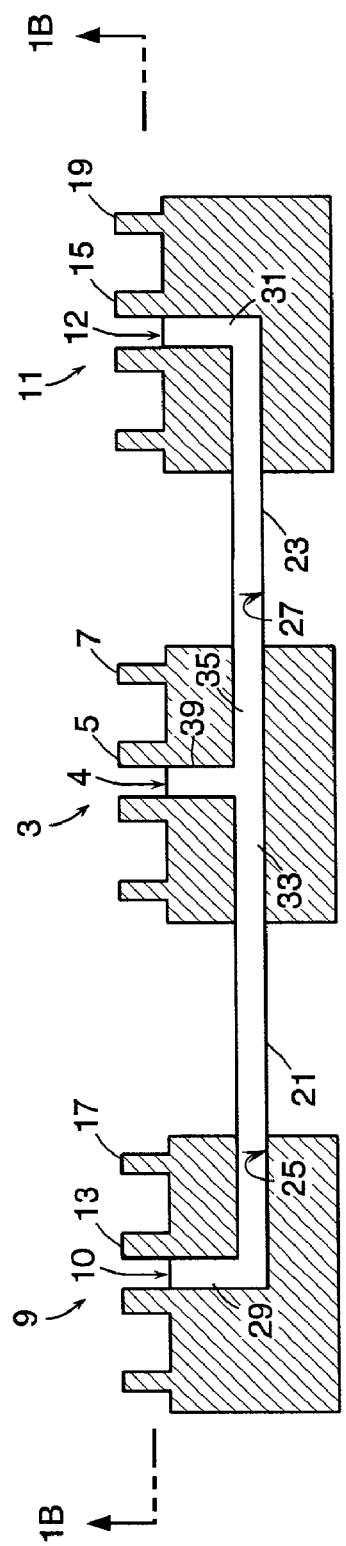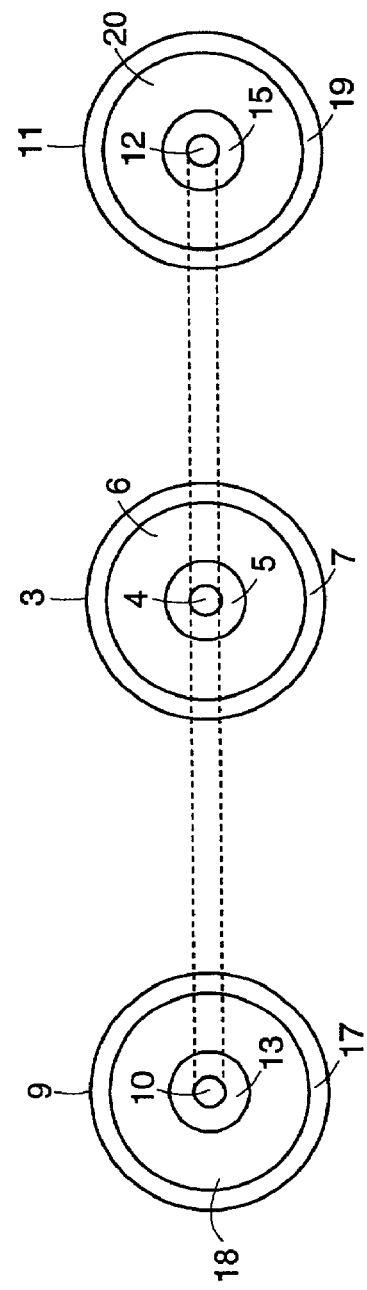
FIG. 1A
FIG. 1B

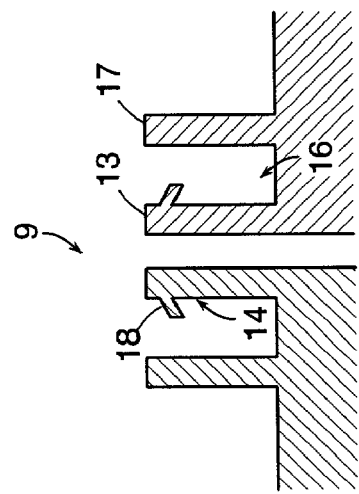
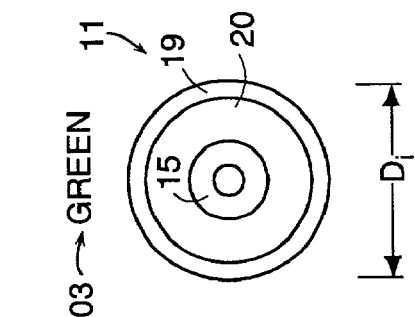
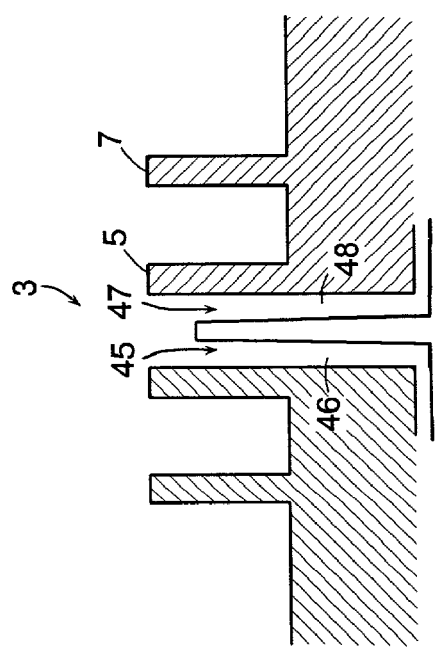
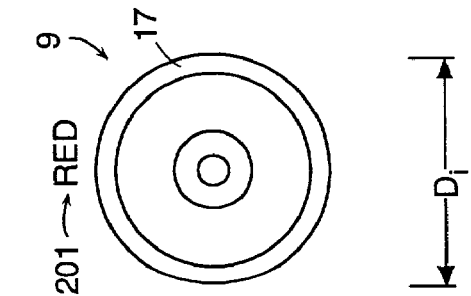

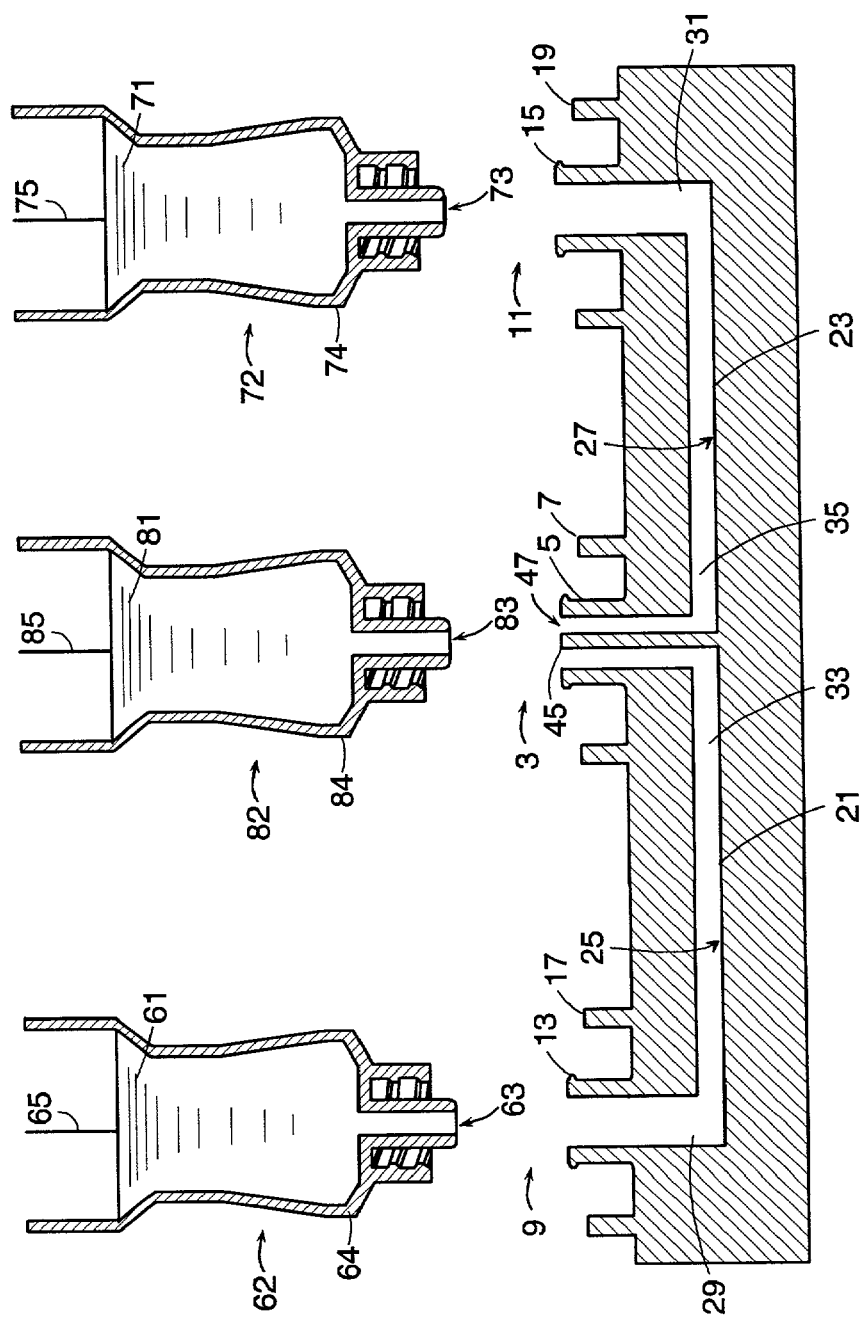

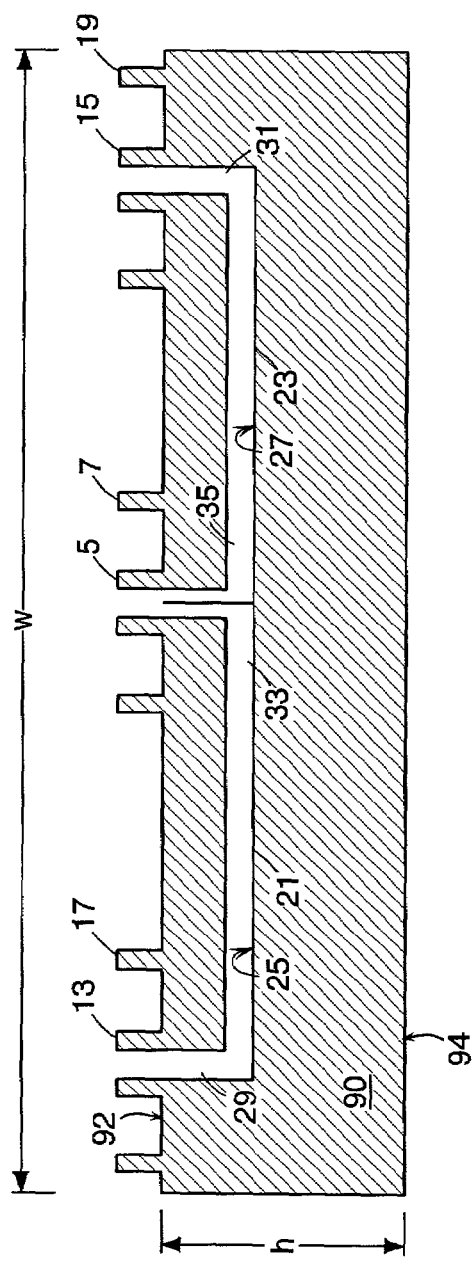
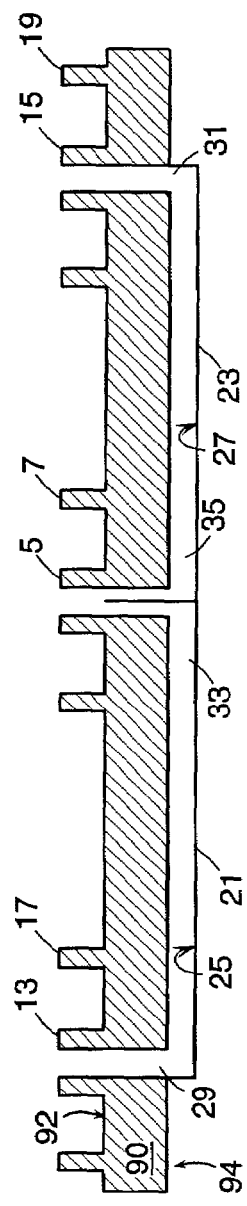
FIG. 7A
FIG. 7B

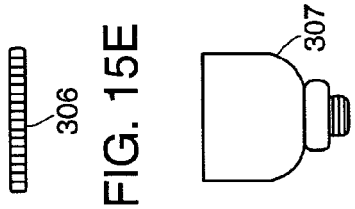
FIG. 15E
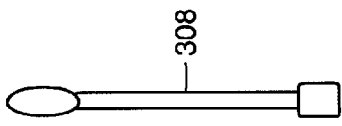
FIG. 15F
FIG. 15G
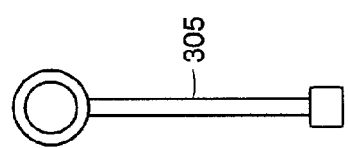
FIG. 15C
FIG. 15D
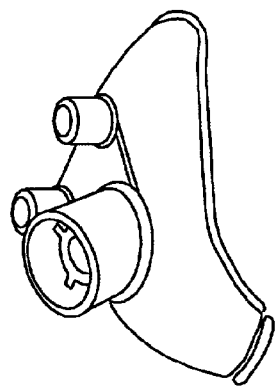
FIG. 15I
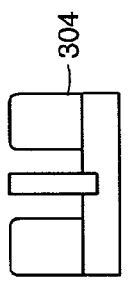
FIG. 15B
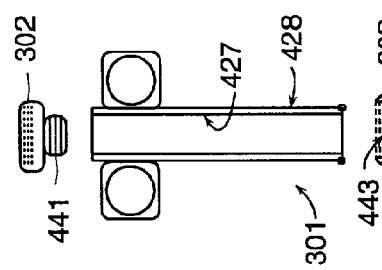
FIG. 15A
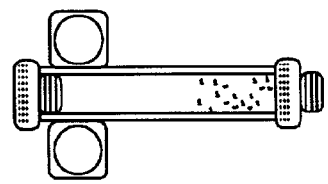
FIG. 15H

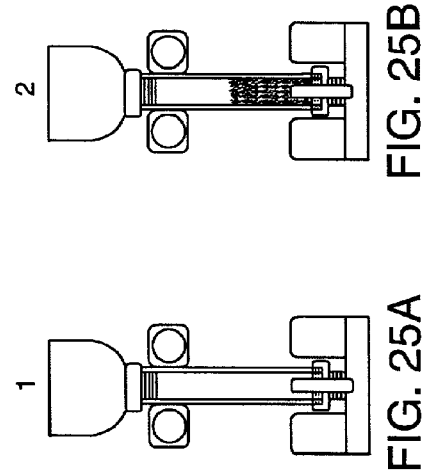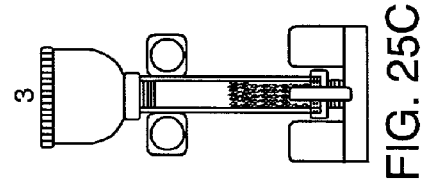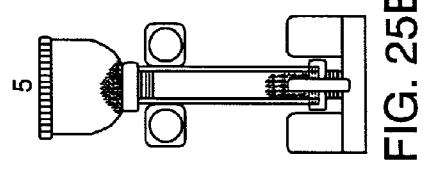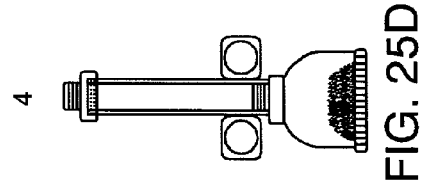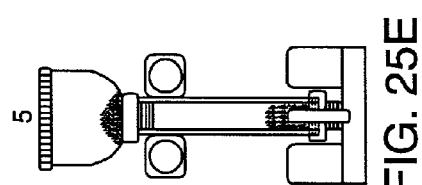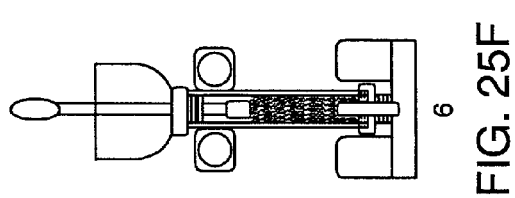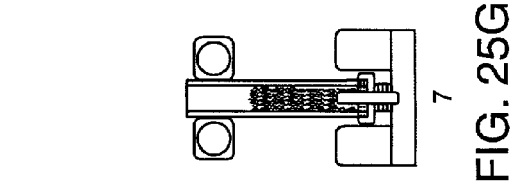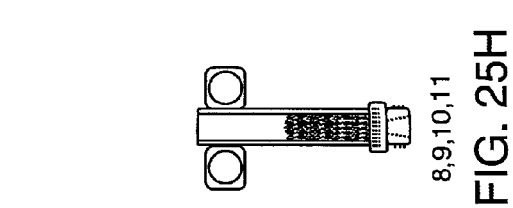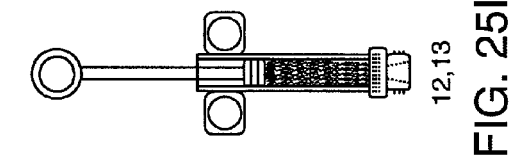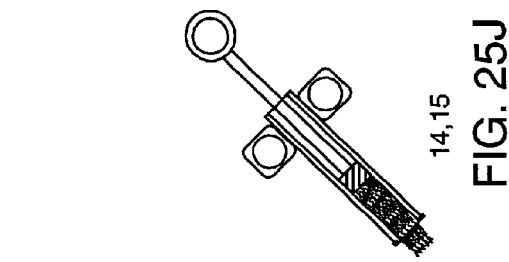

GRAFT DELIVERY SYSTEM

BACKGROUND OF THE INVENTION

When a posterior or posterior-lateral fusion of selected spinal facet joints is desired, the surgeon may seek to enhance the fusion of these joints by placing a gel compound comprising graft material (such as autograft bone chips) and platelet-rich plasma ("PRP") alongside the spinal ridges adjacent to the facet joints. The autograft bone chips contain matrix molecules and living cells such as osteoblasts, and the platelets in the PRP contain additional growth factors which facilitate fusion.

Procedures have been developed for producing this gel. For example, in one conventional process for making the bone chip/platelet-containing gel, the bone chips are placed in a small petri dish, and a 10:1 volumetric mixture of PRP and thrombin (a coagulation agent) is sprayed onto the bone chips. The fibrinogen in the PRP reacts with the thrombin to form clot-producing fibrin, thereby forming a clotted gel. Although this conventional process has been adopted by some surgeons, it nonetheless suffers from some drawbacks. For example, since the desired gel is produced in a flat dish, and not a syringe, it has a shape which is not preferred for facet fusion. In addition, since the dish is typically fairly open, the gel is in a relatively unprotected place. The spraying technique may also produce an uneven gel, thereby increasing the likelihood of open spaces. In addition, since the gel must ultimately be transferred from the dish, there is a risk that the clots in the gel will break. This is undesirable because breakage raises the possibility that the gel will migrate from the intended treatment location.

Figure 13A:
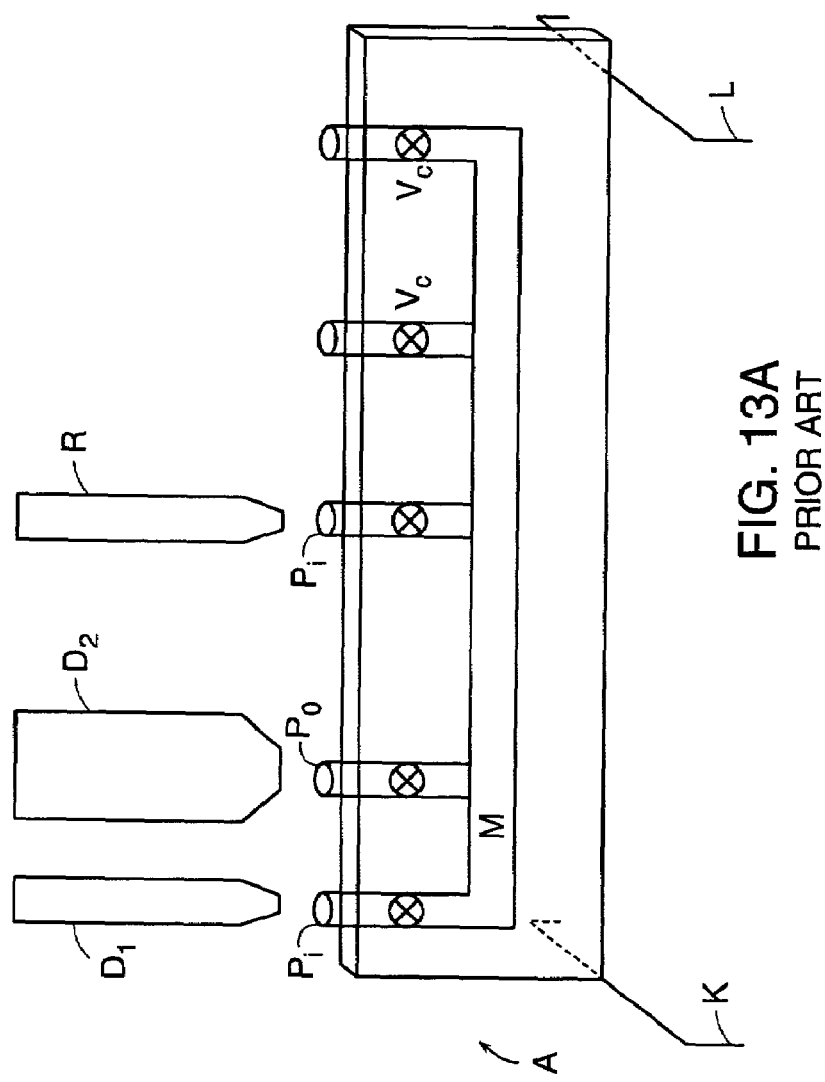

One conventional process seeks to avoid this problem by producing the gel within a syringe. FIG. 13a discloses a five port manifold A for delivering the PRP and thrombin precursors directly into a single receiving syringe R. In this process, two input ports $P_i$ are randomly chosen to respectively receive one delivery syringe containing the PRP and one delivery syringe containing thrombin. Valves V associated with the non-selected ports are closed, and the precursor fluids within the delivery syringes $D_1$ and $D_2$ are emptied into the selected input ports. The precursor fluids travel through tubes within the manifold interior M and enter the receiving syringe R through a randomly selected output port $P_o$ to produce a gelled log of bone graft material. The manifold is typically stabilized by detachable legs K and L, and its ports are colinear.

One problem with using the conventional manifold of FIG. 13a is that the random nature of port selection within the five port manifold can lead to undesirable clotting within the manifold. For example, in the system shown in FIG. 13b, the two input ports B and C are randomly chosen to respectively receive syringe D containing the PRP and syringe E containing thrombin. Valves F and G from the non-selected ports are closed, and the fluids within the delivery syringes D and E are emptied into the ports B and C. As these precursor fluids travel through tube H, each passes through tube section N, thereby providing conditions favorable to clotting in tube section N. These conditions could inhibit the free flow of precursor materials through the manifold.

In addition, since it is common to require production of multiple logs of clotted gel per surgical procedure, it is desirable for the manifold to be free of clots not only during production of gel for the initial syringe, but also during gel production for additional syringes as well. However, the conventional manifold is also susceptible to clotting during subsequent procedures. For example, suppose the ports are fortuitously selected in a manner which avoids the above-mentioned instantaneous clotting problem during production of the initial gel. Such a selection is shown in FIG. 13c. Ports C and Z in FIG. 13c are selected for respective delivery of the PRP and thrombin fluids from syringes E and D to the output port J to produce the first gel log. However, during the production of this gel, tube sections N and O respectively become contaminated with PRP and thrombin. If, for production of the second gelled log, ports Q and B are then selected for respective delivery of the PRP and thrombin fluids to output port J, then the PRP-contaminated tube section N and the thrombin-contaminated tube section P will respectively combine with the thrombin from port B and the PRP from port Q, thereby causing undesired clotting in both of tube sections N and O. These clots in the manifold inhibit the flow of PRP and thrombin in the subsequent procedures.

Figure 13B:
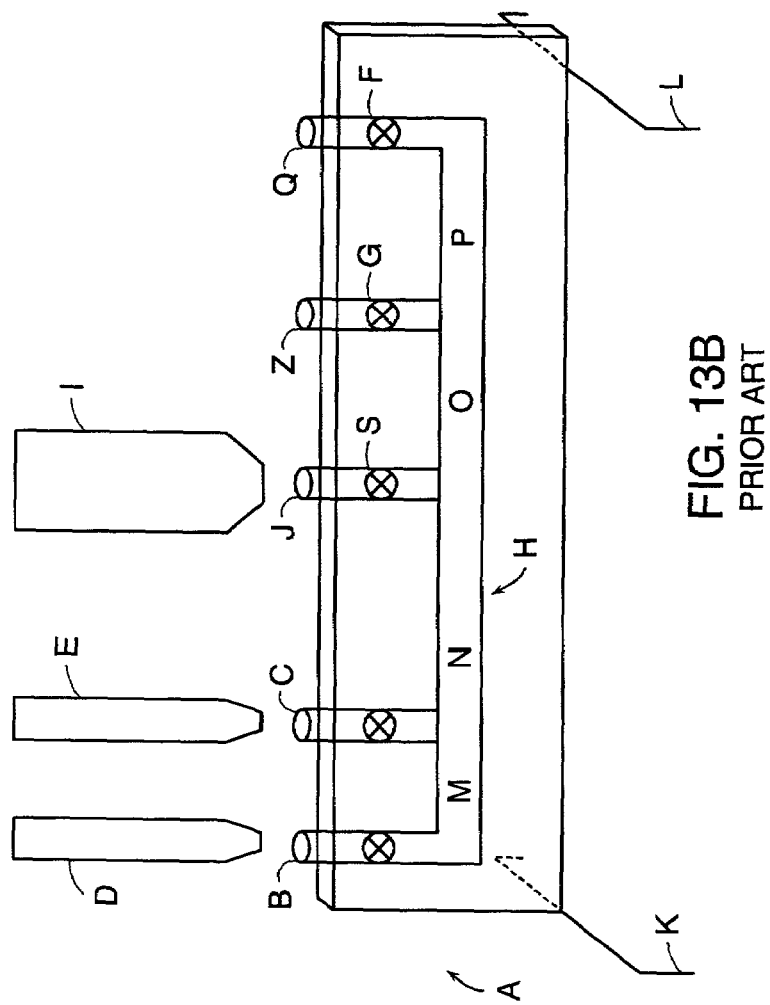
Figure 13C:
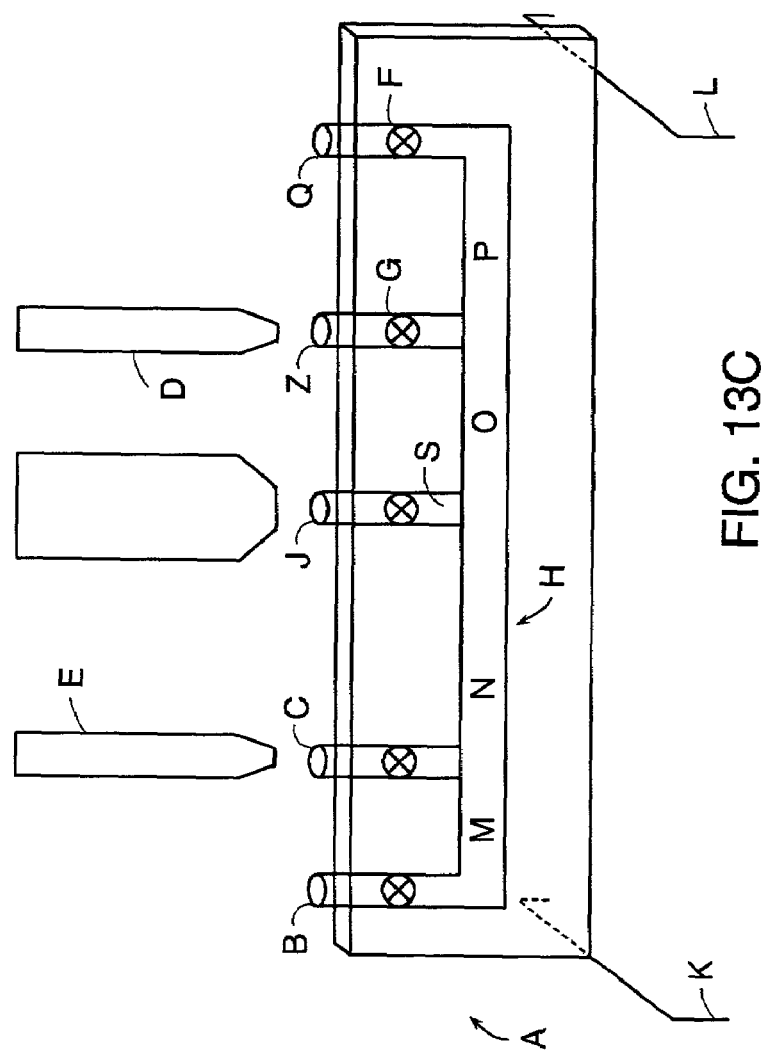

Moreover, even if the three active ports are deliberately selected such that the output port is always between the two input ports (e.g., the system of FIG. 13b is selected and used for all four gel production procedures), there remains a problem in that the PRP and thrombin necessarily meet within tube section S of the manifold, thereby causing clotting within the manifold.

Thus, there is a need for a manifold suitable for producing a gelled log of bone graft material and which minimizes intra-manifold clotting.

Another problem with the conventional manifold shown in FIG. 13 lies in its stability. Applying conventional levels of force to the manifold during fluid delivery may often cause the manifold to tilt, despite the presence of stabilizing legs K and L. Thus, there is a need for a more stable manifold.

Lastly, the tubes within the manifold used in the process of FIG. 13c are often relatively large. For example, there may be about 0.4 cc of tubing between input port Z and output port J. Since a typical delivery syringe will contain only about 1 cc of thrombin, a significant volume of thrombin precursor material may never reach the receiving syringe R. In this case, the 0.4 cc lost volume may represent at least 40% of the PRP. Moreover, if the thrombin delivery syringe is not completely filled or if a non-adjacent output port is selected, the lost volume percentage may be even higher. Likewise, in a typical syringe delivering about 5 cc PRP, the lost volume of PRP in this manifold may be about 8%.

U.S. Pat. No. 5,935,437 discloses an apparatus for filtering blood plasma from whole blood, comprising three syringes in fluid communication with each other via tubes in a manifold, and a membrane housed within the tubes for selectively removing platelets from the blood. Whitmore discloses pores in the membranes filters of 0.2 and 0.55 microns (μm), and states that the pore size may or may not exclude platelets, which typically have a diameter of no more than about 2–3 um.

U.S. Pat. Nos. 4,735,616; 4,978,336; and 5,368,563 each disclose an apparatus useful for producing and administering fibrin glue. Each apparatus includes two syringes, each syringe containing a single glue precursor and received on a first side of a manifold, and an outlet on the opposite side of the manifold adapted for spraying the glue or glue precursors onto a target site.

U.S. Pat. No. 5,116,315 ("Capozzi") describes a syringe system comprising a pair of syringes for delivering biological fluids through a manifold having a pair of ports for the attachment of the syringes, and flanges for attachment of either a spray assembly 20 or a needle assembly 18. Neither assembly is designed for retaining the fluids delivered from the syringes, but rather for expelling the fluids through a spray opening. Consequently, the volume defined by the manifold tubing 50 and 52 appears to be much greater than the volume defined by the spray assembly mixing space 84. The volume of the mixing space 84 appears to be less than 1 cc.

Therefore, it is an object of the present invention to provide a apparatus for mixing and retaining biological fluids comprising a manifold which minimizes intra-manifold mixing of the fluids. In addition, when the fluids comprise gel precursors, there is a particular need for minimizing intra-manifold clotting.

SUMMARY OF THE INVENTION

In one embodiment of the invention, the present invention comprises a manifold suitable for delivering PRP and thrombin to a fluid retention chamber, wherein the manifold comprises only two input ports. By providing only two input ports, the operating procedure is simplified because there is no need for the surgeon to open and close valves. Dedication also reduces the possibility of intra-manifold clotting.

Therefore, in accordance with the present invention, there is provided an apparatus comprising a fluid retention chamber having an opening, and a manifold comprising:

a) an output port adapted for attachment to a fluid retention chamber, the port having at least one opening, b) first and second input ports, each port adapted for attachment to a delivery syringe, each input port having an opening, and c) first and second tubes, each tube having a sterile inner surface, and entry and exit portions, the entry portion of the first tube being in fluid communication with the opening of the first input port, the entry portion of the second tube being in fluid communication with the opening of the second input port, the exit portion of each tube being in fluid communication with the at least one opening of the output port, the at least one opening of the output port of the manifold being in fluid connection with the opening in the fluid retention chamber, wherein the first and second tubes define a tubing volume and the fluid retention chamber defines a retention volume, wherein the retention volume is greater than the tubing volume, wherein the manifold comprises only two input ports, and wherein at least one tube (and preferably each tube) has an effective diameter of at least 10 μm (microns).

DESCRIPTION OF THE FIGURES

FIG. 1*a* is a cross-sectional side view of the manifold of the present invention.

FIG. 1*b* is a cross-sectional aerial view of the manifold of FIG. 1*a*.

FIG. 2 is a cross-sectional side view of an output port of the present invention.

FIG. 3 is a cross-sectional side view of an input port of the present invention.

FIG. 4 is an aerial view of a portion of the upper surface of the present invention.

FIG. 5 is a cross-sectional side view of an apparatus of the present invention.

FIG. 6*a* is an aerial view of a portion of the upper surface of the manifold of the present invention.

FIG. 6*b* is a schematic representation of the angles formed by the ports of FIG. 6*a*.

FIGS. 7*a* and 7*b* are cross-sectional side views of preferred embodiments of the manifold of the present invention.

FIG. 8*a* is a perspective view of a preferred embodiment of the manifold of the present invention.

FIG. 8*b* is a cross-sectional side view of a portion of FIG. 8*a*.

FIG. 9*a* is a perspective view of one manifold of the present invention.

FIGS. 9*b* and 9*c* are cross sections of preferred ports.

FIG. 10 is a perspective view of a manifold of the present invention.

FIG. 11 is a cross-sectional side view of FIG. 8*a*.

FIG. 12*a* is a perspective view of a manifold of the present invention.

FIG. 12*b* is an aerial view of FIG. 12*a*.

FIG. 12*c* is a schematic representation of the angles formed by the legs of FIG. 12*a*.

FIGS. 13*a–c* present perspective views of a prior art manifold having delivery and receiving syringes received therein.

FIG. 14 is a prespective view of the tube portion of a fluid retention chamber having an intervertebral cage disposed therein.

FIGS. 15*a–i* are perspective views of different components of the apparatus of the present invention.

FIGS. 16*a* and *b* are perspective views of a fluid retention chamber of the present invention.

FIG. 17 is a perspective view of a fluid retention chamber comprising a plunger, along with a tube portion of a fluid retention chamber.

FIG. 18*a* is a perspective view of a plunger of the present invention.

FIG. 18*b* is a cross section view of an end cap of the present invention.

FIGS. 19*a–d* are perspective views of a two piece manifold connector.

FIG. 19*e* is a cross sectional view of the two piece manifold connector.

FIG. 20 is a perspective view of a manifold of the present invention.

FIG. 21 is a perspective view of a manifold of the present invention.

FIG. 21*a* is a perspective view of a portion of the output port of FIG. 21.

FIG. 22 is a perspective view of a connector attachable to the output port of FIG. 21*a*.

FIGS. 23*a* and *b* are respective cross sectional side and aerial views of a manifold connector of the present invention.

FIG. 23*c* is a perspective view of a dual lumen assembly.

FIGS. 24*a* and 24*b* are perspective views of graft forceps.

FIGS. 25*a–j* depict steps in using the present invention.

FIGS. 26 and 27 are perspective views of the apparatus of the present invention.

DETAILED DESCRIPTION OF THE INVENTION

For the purposes of the present invention, the thrombin and PRP fluids are collectively referred to herein as "the precursor fluids". Determination of "the first X % of a tube"

selects the entry opening of the associated input port as the starting point of the tube. "Attachment" contemplates intermediate connector pieces. A "lost volume fraction" is the volume of a manifold tube (from the input port to the output port) divided by the volume of the associated delivery syringe.

For the purposes of the present invention, the "effective diameter" of a tube represents the diameter of the largest particle which can pass through the tube. For example, a tube having a nominal inner diameter of 1 mm in which a membrane having a pore size of 10 um is disposed has an effective diameter of 10 um because particles greater than 10 um will be stopped by the membrane.

In one preferred embodiment, and now referring to FIG. 1a, there is provided a manifold 1 comprising:
  a) an output port 3 adapted for attachment to a fluid retention chamber, the port having at least one opening 4,
  b) first and second input ports (9,11), each port adapted for attachment to a delivery syringe, each input port having an opening (10,12), and
  c) first and second tubes (21,23), each tube having a sterile inner surface(25,27), and entry (29,31) and exit (39,39) portions, the entry portion of the first tube being in fluid communication with the opening of the first input port, the entry portion of the second tube being in fluid communication with the opening of the second input port, the exit portion of each tube being in fluid communication with the at least one opening of the output port.

In this embodiment, the configuration of output port 3 comprises inner annulus 5, a co-axial outer annulus 7, and an inner surface 6 therebetween. The configurations of input ports 9,11 comprise an inner annulus 13,15, a co-axial outer annulus 17,19, and an inner surface 18,20 therebetween. During use, the precursor delivery syringes may be attached to the input ports by placing them into the recess formed by the respective co-axial annuli.

In the embodiment presented in FIG. 1a, each tube shares exit portion 39 which opens into exit opening 4 of the output port. Although this embodiment solves the clotting problems along a significant portion of the tubes, it nonetheless still does not prevent the mixing of precursor fluids in exit tube portion 39, and so there is still some risk of intra-manifold clotting. Accordingly, in some embodiments, at least 30% of at least one of the tubes is dedicated. Preferably, at least 30% of each tube is so dedicated. When the length of shared tubing is controlled, there is a relatively small path over which the precursor fluids combine prior to exiting the manifold, thereby controlling intra-manifold clotting. Preferably, the dedicated fraction of each tube is at least 40%, more preferably at least 60%, more preferably at least 90%, more preferably at least 95%. In FIG. 1a, first tube 21 is "dedicated" from entry portion 29 to portion 33, while second tube 23 is "dedicated" from entry portion 31 to portion 35. Therefore, about the first 75% of each tube in FIG. 1 is dedicated.

Therefore, in accordance with the present invention, there is provided an apparatus comprising a fluid retention chamber having an opening, and a manifold comprising:
  a) an output port adapted for attachment to a fluid retention chamber, the port having at least one opening,
  b) first and second input ports, each port adapted for attachment to a delivery syringe, each input port having an opening, and
  c) first and second tubes, each tube having a sterile inner surface, and entry and exit portions, the entry portion of the first tube being in fluid communication with the opening of the first input port, the entry portion of the second tube being in fluid communication with the opening of the second input port, the exit portion of each tube being in fluid communication with the at least one opening of the output port, the at least one opening of the output port of the manifold being in fluid connection with the opening in the fluid retention chamber, wherein the first and second tubes define a tubing volume and the fluid retention chamber defines a retention volume, wherein the retention volume is greater than the tubing volume, wherein at least the first 30% of the first tube is dedicated.

Although providing dedicated portions of tubing minimizes the undesired mixing of precursor fluids within the manifold, there is still some risk of intra-manifold clotting, particularly within shared exit tube portion 39. Therefore, in another preferred embodiment, and now referring to FIG. 2, the sharing of an exit tube portion is eliminated and the respective tubes are completely dedicated. During use, the respective precursor fluids empty into different openings in the output port 3, thereby preventing any mixing of the precursor fluids within the manifold. In particular, the output port 3 comprises first 45 and second 47 openings, and exit portion 46 of the first tube opens into the first opening 45, and exit portion 48 of the second tube opens into the second opening 47.

Therefore, in accordance with the present invention, there is provided an apparatus comprising a fluid retention chamber having an opening, and a manifold comprising:
  a) an output port adapted for attachment to a fluid retention chamber, the port having at least one opening,
  b) first and second input ports, each port adapted for attachment to a delivery syringe, each input port having an opening, and
  c) first and second tubes, each tube having a sterile inner surface, and entry and exit portions, the entry portion of the first tube being in fluid communication with the opening of the first input port, the entry portion of the second tube being in fluid communication with the opening of the second input port, the exit portion of each tube being in fluid communication with the at least one opening of the output port, the at least one opening of the output port of the manifold being in fluid connection with the opening in the fluid retention chamber, wherein the first and second tubes define a tubing volume and the fluid retention chamber defines a retention volume, wherein the retention volume is greater than the tubing volume, wherein the output port has distinct first and second openings, the first opening being in fluid connection with the exit portion of the first tube, and the second opening being in fluid connection with the exit portion of the second tube.

In some embodiments of the present invention, the tubing diameter and length is selected so that the volume of at least one manifold tube is less than 0.3 cc, preferably less than 0.1 cc. For purposes of illustration, second manifold tube 23 begins at entry opening 12 and ends at exit opening 4. In some embodiments of the apparatus using a thrombin delivery syringe having a 1 cc volume, the tubing carrying the thrombin has a volume of about 0.05 cc. Thus, the lost volume fraction of this embodiment is about 5%, and the manifold efficiently converts thrombin to gel. In some embodiments of the apparatus using a PRP delivery syringe having a 10 cc volume, the tubing carrying the PRP has a volume of about 0.5 cc. Thus, the lost volume fraction is again about 5%, and the manifold efficiently converts PRP to gel. Preferably, the lost volume fraction associated with each tube is less than 35%, more preferably less than 20%, most preferably less than 10%.

Generally, the effective diameter of the tube portion of the present invention should be sufficient to pass nucleated human cells. In applications involving PRP, the minimum effective diameter is thought to be at least about 10 um. However, in certain applications such as those using bone marrow aspirate, the cells therein are somewhat larger and so the effective diameter of the tubing should be at least 100 um, more preferably, at least 250 um, most preferably at least 500 um.

In some embodiments, the first tube has an effective diameter of about 1.143 mm and the second tube has an effective diameter of about 0.635 mm.

In some embodiments, the effective diameter of at least one tube is 10 um. This sizing is believed to be suitable for passing fluids such as PRP. However, in other embodiments targeted for mixing other fluids, it may be preferable to use tubing having a larger effective diameter. For example, in applications targeted for the mixing of bone marrow aspirate (or suspensions thereof), at least one manifold tube has an effective diameter of at least 40 um.

In some embodiments, it may be desirable to tailor the diameters of the respective first and second tubes so that each delivers fluids at a desirable predetermined ratio. For example, in the case of PRP and thrombin, when a 10:1 volumetric mixing ratio is desired, it is preferable for the tube delivering the PRP to have a greater diameter than the tube delivering the thrombin. When the diameters are so controlled, simultaneous actuation of the delivery syringe plungers can produce the desired 10:1 flow rates of the respective fluids into the fluid retention chamber, thereby providing the 10:1 ratio desirable for mixing. In some embodiments, the first tube (preferably for delivering PRP) has a diameter at least 20% greater than (and more preferably at least 50% greater than) the diameter of the second tube (preferably containing thrombin). In some instances this is practicably provided by making the second tube very small. For example, in one embodiment, the second tube has an inner diameter of less than 1 mm, more preferably less than about 0.8 mm.

In another preferred embodiment, and now referring to FIG. 3, at least one input port 9 has a luer lock fitting 16 in which the inner annulus 13 has at least one flange 18 extending from its outer wall 14. The luer lock fitting is a standard fitting used for connecting the threaded inner wall of a syringe to a port, thereby making the manifold of the present invention easily adaptable for use in biomedical applications.

Since the configurations of the input and output ports in FIG. 1 are substantially identical, there may be a danger that the user could mistakenly fit the fluid retention chamber to input port 9, causing each precursor fluid to flow through common tube portion 21. Therefore, there is a need to visually distinctively identify the output port. Accordingly, there is provided an apparatus comprising a fluid retention chamber having an opening, and a manifold comprising:

a) an output port adapted for attachment to a fluid retention chamber, the port having at least one opening,
b) first and second input ports, each port adapted for attachment to a delivery syringe, each input port having an opening, and
c) first and second tubes, each tube having a sterile inner surface, and entry and exit portions, the entry portion of the first tube being in fluid communication with the opening of the first input port, the entry portion of the second tube being in fluid communication with the opening of the second input port, the exit portion of each tube being in fluid communication with the at least one opening of the output port, the at least one opening of the output port of the manifold being in fluid connection with the opening in the fluid retention chamber, wherein the first and second tubes define a tubing volume and the fluid retention chamber defines a retention volume, wherein the retention volume is greater than the tubing volume, wherein at least one port is visually distinctive from the remaining ports.

In one preferred embodiment, and now referring to FIG. 4, the output port is distinctive. In particular, the diameter Do of the output port is different than the diameter Di of at least one input port. When the delivery and receiving ports have different diameters, the user can more readily identify the port intended to be the output port, and the chances of mistaken selection by the user are minimized.

In some embodiments, delivery syringes $D_1$ and $D_2$ are relatively small (1 and 10 cc) and have a small barrel (9.3 and 16 mm), while the fluid retention chamber R is relatively large (15–30 cc) and has a relatively large barrel 20 mm. Therefore, in order to accommodate these size differences, in another preferred embodiment, the diameter Do of the output port is larger than the diameter Di each input port. This embodiment not only provides the distinction advantage described directly above, but also provides desirable sizing correspondence with preferred fluid retention chambers and delivery syringes. Preferably, the ratio of the diameter Do of the output port to the diameter Di of the input port is at least 2:1. More preferably, the ratio is at least 3:1.

In another embodiment, the input ports are provided with luer lock fittings while the output port has no luer lock fitting. This also provides distinction.

In some embodiments, the attachment of the fluid retention chamber to the receiving port is characterized by a reverse luer connection. That is, in some embodiments, the output port of the manifold is characterized by male luer fitting, and the fluid retention chamber has a female luer fitting. This embodiment provides at least one advantage by further differentiating the output and input ports, thereby minimizing the chances of mistaken port selection.

Also in FIG. 4, the two input ports are distinctly marked. In particular, input port 9 is marked with a first set of characters 201 (in this case "RED") while input port 11 is marked with a second set of characters 203 (in this case "GREEN"). Distinction may be provided by any conventional means, such as color coding with different colors or by distinctive characters. Therefore, in this configuration of FIG. 4, the larger diameter of the receiving port provides assurance that this port will be correctly identified as such, and the distinct marking of the delivery ports insures that, during subsequent procedures, each will be correctly used for delivery of the desired precursor fluid.

If multiple logs of gel are to be created, then it is desirable to insure that the thrombin-containing syringe is inserted into the same input port each time in order to prevent multiple use coagulation. Since conventional process typically use PRP and thrombin in a volume ratio of about 10:1, in some embodiments, the delivery syringe barrel containing the thrombin precursor will typically be thinner than the delivery syringe containing the PRP. Therefore, in some embodiments, one input port will have a configuration designed to accommodate only narrow syringes and the other input port will have no such restriction. This can be accomplished by providing the input port for the thrombin syringe with an outer annulus 19, thereby defining a narrow recess 20 between the co-axial annuli, as in FIG. 4. The diameter of this outer annulus 19 is selected such that the narrow recess can accommodate the outer wall of the thinner thrombin-containing syringe, but will act as a stop against the PRP-containing syringe. In one embodiment, each input port 9 and 11 also have outer annuli with different diameters 205 and 207 which respectively provide attachment for the openings of 10 cc and 1 cc syringes—thereby insuring that input port 11 will be used only for the delivery of thrombin, and input port 9 will be used only for the delivery of PRP.

In some embodiments, when the PRP delivery tubing is substantially isolated from the thrombin delivery tubing, the manifold may have more than three ports without substantially increasing the intra-manifold clotting concerns. In one such embodiment, the manifold has five ports—one receiving port and four delivery ports. In this embodiment, two sets of delivery syringes can be used at the same time, thereby shortening by one-half the time required to fill a receiving syringe.

In another embodiment, more than two fluids are delivered within the manifold and mixed in the fluid retention chamber. For example, in one embodiment, three input ports separately receive respective syringes filled with PRP, bone marrow aspirate and a coagulation agent such as thrombin.

Now referring to FIG. 5, there is provided a preferred method of using the manifold of the present invention. Bores 61 and 71 of delivery syringes 62 and 72 are respectively filled with PRP and thrombin, and are inserted into respective input ports 9 and 11. In particular, the annular walls 64 and 74 formed by syringe openings 63 and 73 are inserted into the recess between the inner (13,15) and co-axial outer (17,19) annuli of each input port.

Similarly, fluid retention chamber 82 having an empty bore 81 is likewise inserted into input port 3. In particular, the annular wall 84 formed by opening 83 is inserted into the recess formed between the inner 5 and co-axial outer 7 annulus of the input port 3.

Next, plungers 65,75 of the delivery syringes 62,72 are simultaneously depressed and the precursor fluids are advanced through openings 63 and 73 and into the manifold via tubes 21,23. The fluids advance through the tubes, exit through port openings 45,47, and advance into the opening 83 of fluid retention chamber 82 (which may optionally container bone particles (not shown)). As the fluids meet in bore 81, they begin to gel to from the desired log. Once the precursor fluids in the delivery syringes have been delivered into the fluid retention chamber, it is preferable to wait about 3–5 minutes to allow the precursor materials in the receiving syringe to adequately gel. After this waiting period has lapsed, fluid retention chamber 82 is removed from output port 3. If desired, this process is then repeated a sufficient number of times to produce multiple logs of gel.

It has been found during use that, when the conventional manifold design of FIG. 13*a* is used, the manifold easily becomes unstable and is prone to tipping. In addition, when the delivery syringes are disposed on opposite sides of the receiving syringe, the user can not easily use one hand to simultaneously acuate each delivery syringe. In order to obviate this problem, in some embodiments, the manifold ports are not co-linear. The non-linear design produces a more stable system which can suitably resist slightly off-center pressures without tipping, and it also allows for simultaneous manual actuation of the delivery syringe pistons. Now referring to FIGS. 6*a* and 6*b*, there is provided an apparatus for mixing biomedical fluids comprising a manifold comprising:
  a) an output port 3 adapted for attachment to a fluid retention chamber, the port having at least one opening,
  b) first and second input ports (9,11), each port adapted for attachment to a delivery syringe, each input port having an opening, and
  c) first and second tubes), each tube having a sterile inner surface, and entry and exit portions, the entry portion of the first tube being in fluid communication with the opening of the first input port, the entry portion of the second tube being in fluid communication with the opening of the second input port, the exit portion of each tube being in fluid communication with the at least one opening of the output port, wherein each opening has a centerpoint 2,12,14, wherein the three centerpoints 2,12 and 14 define a triangle.

Figure 6B:
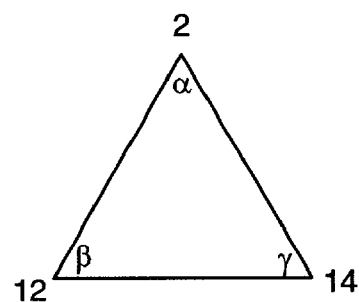

Preferably, and now referring to FIG. 6*b*, the triangle defines three angles $\alpha$, $\beta$ and $\chi$, angle $\alpha$ is the angle formed at output port 3. Preferably, angle $\alpha$ is between 5 and 90 degrees; more preferably between about 5 and 45 degrees; more preferably between about 10 and 30 degrees.

Although the manifold of FIG. 1 effectively solves a number of clotting-related issues, it is not very robust and is prone to twisting during use. Therefore, in another preferred embodiment, the apparatus further comprises a base continuously connecting each port. This base provides the system with rigidity to prevent twisting. In some embodiments, as in FIG. 7*a*, the continuous base 90 has an upper surface 92, wherein each port extends from the upper surface 92 of the base.

Therefore, in some embodiments, the manifold further comprises:
  d) a continuous base having an upper and lower surface, wherein each port is located upon the base.

In some embodiments (as in FIG. 7*a*), the continuous base further comprises a lower surface 94, and the tubes 21 and 23 are conduits formed between the upper and lower surfaces of the base. This design shields the tubes from inadvertent puncture. In another preferred embodiment (as in FIG. 7*b*) in which the base 90 further comprises a lower surface 94, and the tubes 21 and 23 are formed on the lower surface of the base. Preferably, the integral base is substantially circular.

In preferred embodiments, as in FIG. 7*a*, the height H of the base is less than twice the smallest width W of the base (i.e., H/W<2). Controlling the height and smallest width of the base of the manifold in this manner furthers the stability of the apparatus. More preferably, H/W<1, most preferably H/W<0.5.

Therefore, in some embodiments, the manifold further comprises:

d) an continuous base having an upper and lower surface, wherein each port is located upon the base, wherein the base has a height and a width, and wherein the height of the base is less than twice the width of the base.

Figure 8B:
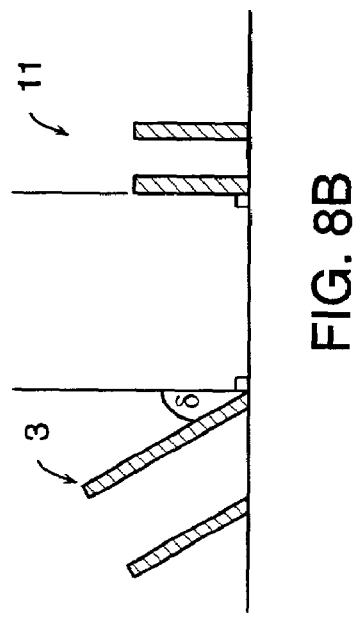
Figure 8A:
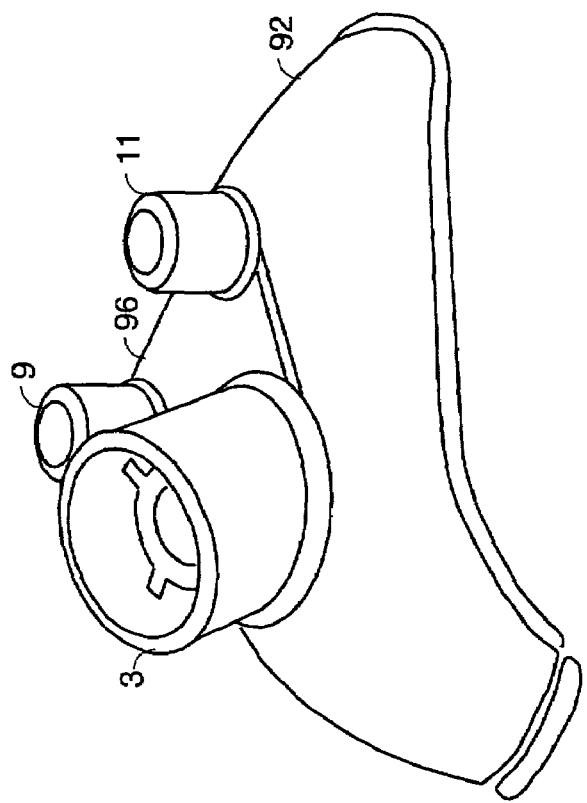

It has also been found during use that, when the manifold design of FIG. 5 is used, the grips of fluid retention chamber 82 (grips not shown) can sometime collide with the delivery syringes as the grips are pulled back from the manifold. Accordingly, as now provided in FIGS. 8a and 8b, in preferred embodiments, the outer annulus of the output port 3 extends from the upper surface 92 of the base at an offset angle δ leading away from a line defining the extension of an input port. In this design, the risk of inadvertent collision with other delivery syringes is minimized. Preferably, the offset angle δ is between 30 and 60 degrees. When the input ports are vertically disposed, the 30–60 degree window provides the fluid retention chamber with adequate clearance from the input delivery syringes, while at the same time minimizing the chances of incomplete mixing within the fluid retention chamber.

Therefore, in some embodiments, the manifold further comprises:

d) an continuous base having an upper and lower surface, wherein each port is located upon the base, wherein the output port extends from the upper surface of the base at an offset angle δ leading away from the input ports.

Figure 9C:
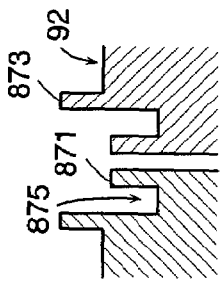
Figure 9A:
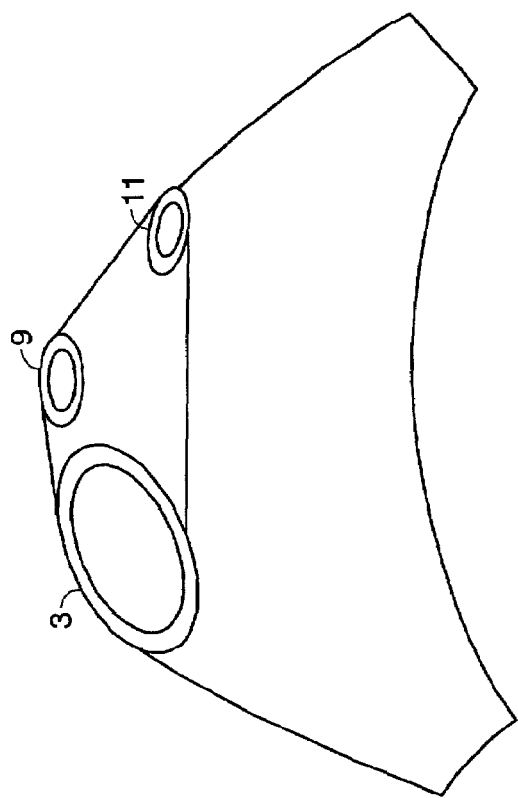
Figure 9B:
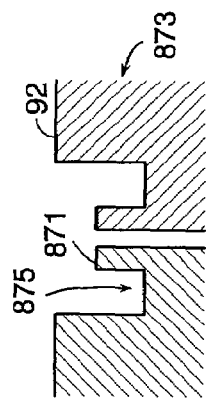

The extending ports of the apparatus may also make the apparatus susceptible to being knocked over by an errant hand. Therefore, in one preferred embodiment, as shown in FIGS. 9a–c, at least one port 3 is at least partially formed between the upper 92 and lower surfaces of the base. The hidden port feature of this embodiment reduces the chances of the apparatus being accidentally tipped.

Therefore, in some embodiments, the manifold further comprises:

d) an continuous base having an upper 92 and lower surface, wherein each port is located upon the base, wherein at least one port comprises an inner annulus 871 and an outer annulus 873, and an inner surface 875 therebetween, and the inner surface 875 of the at least one port is beneath the upper surface of the base. Preferably, the outer annulus 873 does not rise above the upper surface of the base, as in FIG. 9b.

In another embodiment, as shown in FIG. 9c, the outer annulus 873 may extend from the upper surface 92 of the base, the inner surface 875 is sunk beneath the upper surface 92 of the base, and the inner annulus 871 extends from the inner surface 875.

Figure 10:
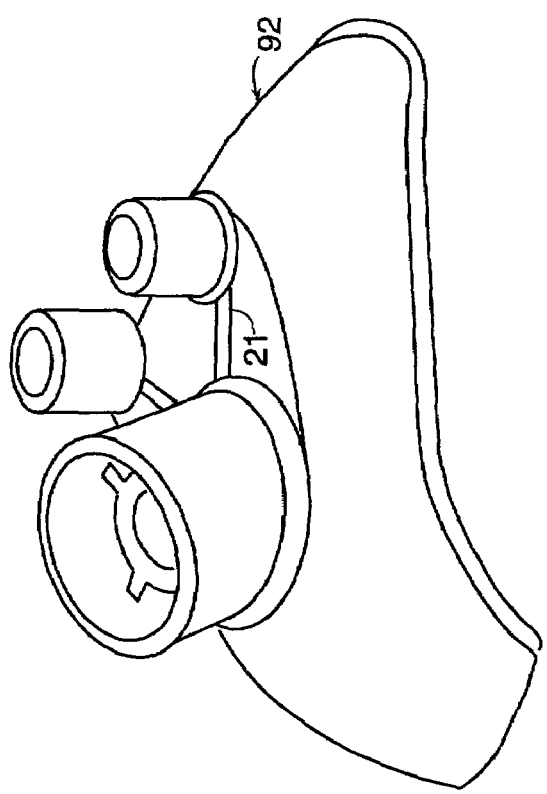

In one preferred embodiment, as shown in FIG. 10, at least a portion of one tube 21 contacts the upper surface 92 of the base, thereby exposing the tube to view from above. When this exposed tube is translucent, the user can visually monitor the flow of the precursor fluids within the tube.

Therefore, in some embodiments, the manifold further comprises:

d) an continuous base having an upper and lower surface, wherein each port is located upon the base, wherein at least a portion of at least one tube is formed upon the upper surface of the base.

Figure 11:
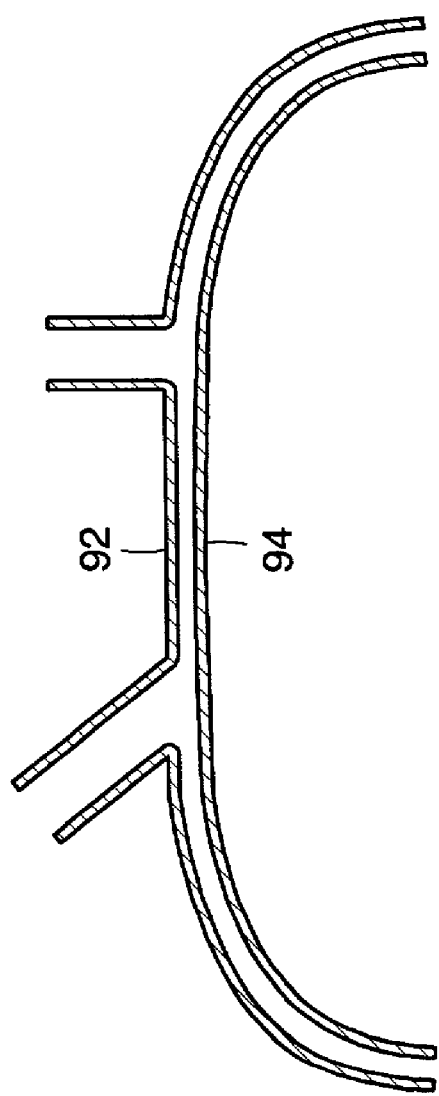

As shown in FIG. 11, in one preferred embodiment of the base having an upper and lower surface, both the upper surface 92 and the lower surface 94 are curved away from the port openings. The design is advantageous in that it provides additional stability to the user, and allows spread of the delivery syringes and fluid retention chamber.

Therefore, in some embodiments, the manifold further comprises:

d) an continuous base having an upper and lower surface, wherein each port is located upon the base, wherein the upper surface is convex.

Figure 12B:
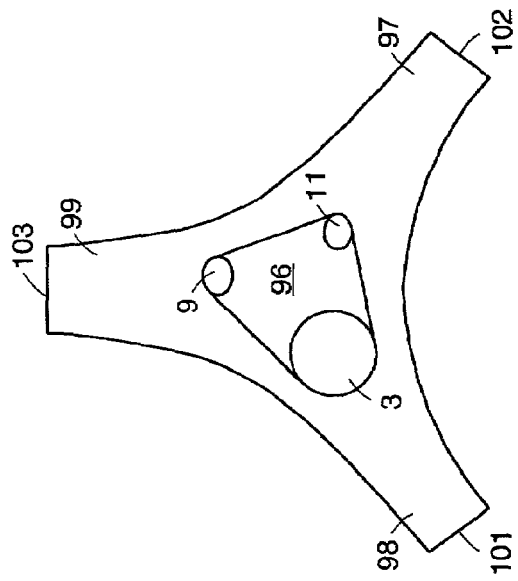
Figure 12C:
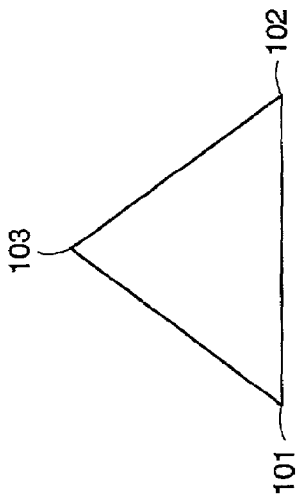
Figure 12A:
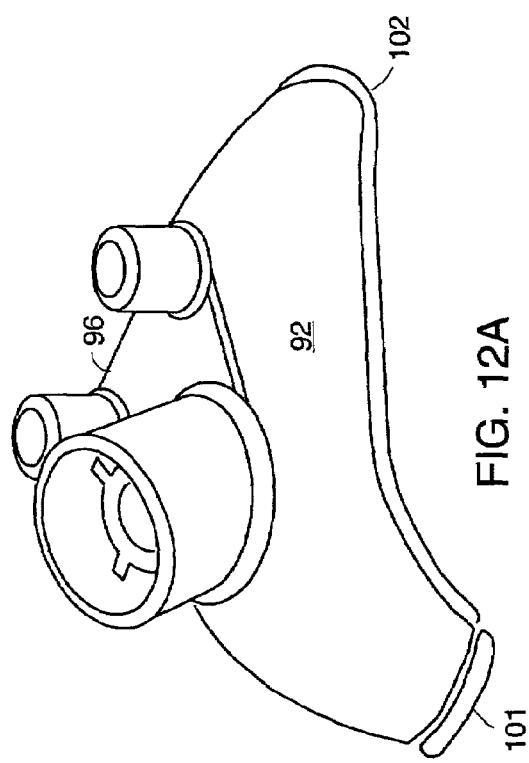

The manifold of FIG. 12a presents an upper surface 92 of the base comprising a central portion 96 which is flat and is located within a first triangle defined by the centerpoints of the ports. This design enhances the stability of the apparatus. The base of this apparatus also comprises three legs 97, 98 and 99 extending from the central portion 96 in substantially the same direction as the first triangle formed by the centerpoints 2, 12 and 14. In one preferred embodiment, each leg also forms an end 101, 102 and 103, the three ends 101–103 defining a triangle Te, wherein the plane defined by triangle Te is parallel to the flat portion 96 of the upper surface of the base.

Therefore, in some embodiments, the manifold further comprises:

d) an continuous base having an upper and lower surface, wherein each port is located upon the base, wherein the upper surface comprises: i) a central portion upon which each port is located, and ii) three legs extending from the central portion.

Figure 20:
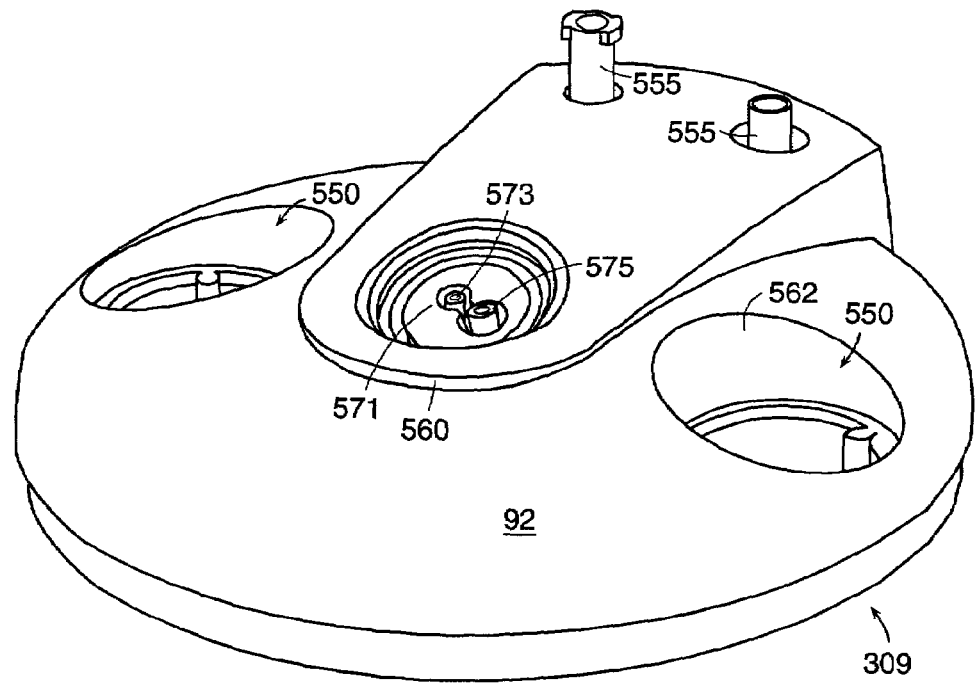

Now referring to FIG. 20, in some embodiments, manifold 309 has a pair of stands 550 designed for reception of the fluid retention chamber to facilitate their filling with graft materials such as bone particles. It further has a pair of input ports 555 fitted with luer lock connections shaped to mate with standard delivery syringes. Lastly, it has a receiving port 560 shaped to attach a selected manifold connector.

In addition to the above-noted use, the gel may also be used in conjunction with orthopaedic hardware device such as prosthetic devices and fusion implants. Fusion implants include intervertebral cages, intervertebral mesh devices, intramedullary rods, screws, and fixation plates. The device may be inserted into the fluid retention chamber prior to gelation. When the precursor fluids enter fluid retention chamber, they also enter the open spaces of the cage, and likewise form a gel therein, thereby producing a gel-filled cage suitable for placing within an intervertebral disc space.

Figure 14:
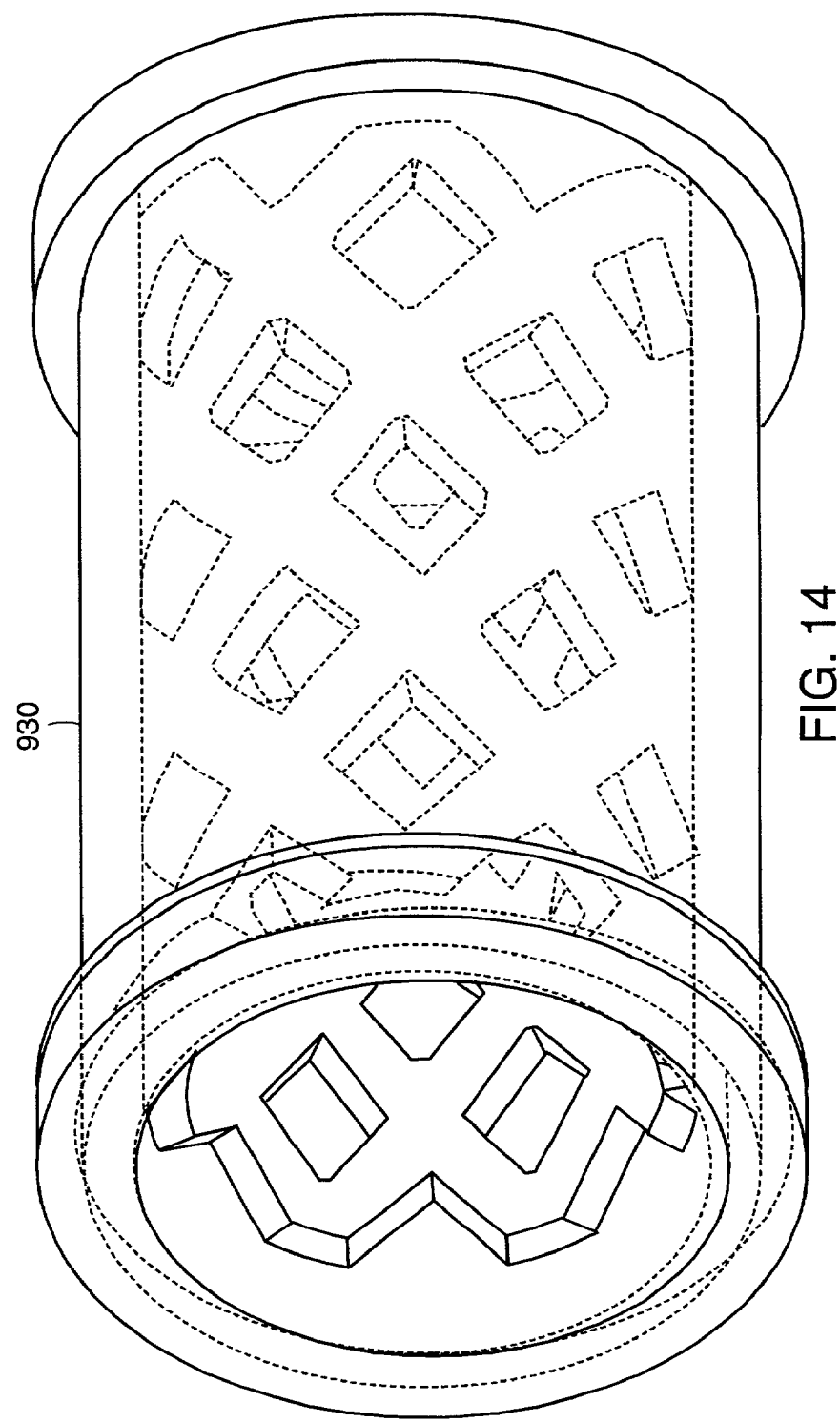

Therefore, in accordance with the present invention, and now referring to FIG. 14, there is provided an apparatus comprising:

a) a fluid retention chamber comprising an opening and having a sterile inner surface, and b) a sterile orthopaedic device disposed within the hollow tube.

Optionally, the device may have porosity which can be pre-filled with bone particles, such as allograft, autograft or demineralized bone matrix (DBM).

In some embodiments, and now referring to FIG. 15, the graft delivery system comprises a number of components useful for preparing and delivering the bone graft. These include: a) fluid retention chamber 301, b) end caps 302, c) manifold connector 303, d) stands 304, e) plunger 305, f) funnel lid 306, g) funnel 307, and h) tamp 308.

Preferably, at least a portion of each component in the apparatus and particular those discussed above is sterile.

More preferably, the entire component is sterile. This can be accomplished by either sterilizing the component at the manufacturing facility, or by providing for terminal sterilization.

Figure 16A:
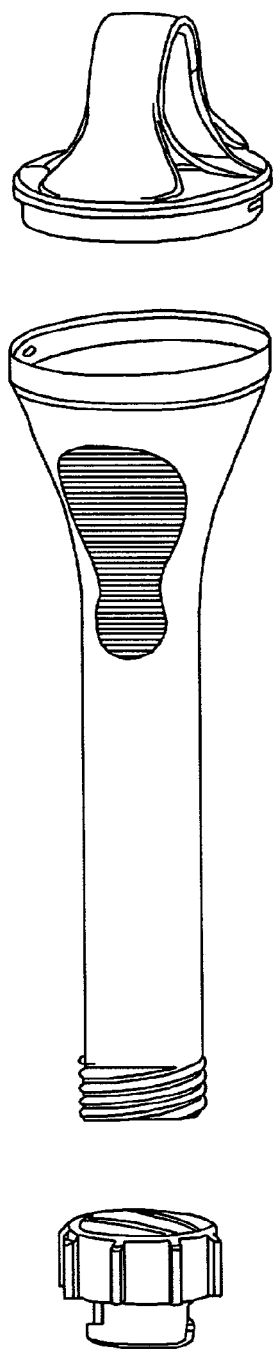
Figure 16B:
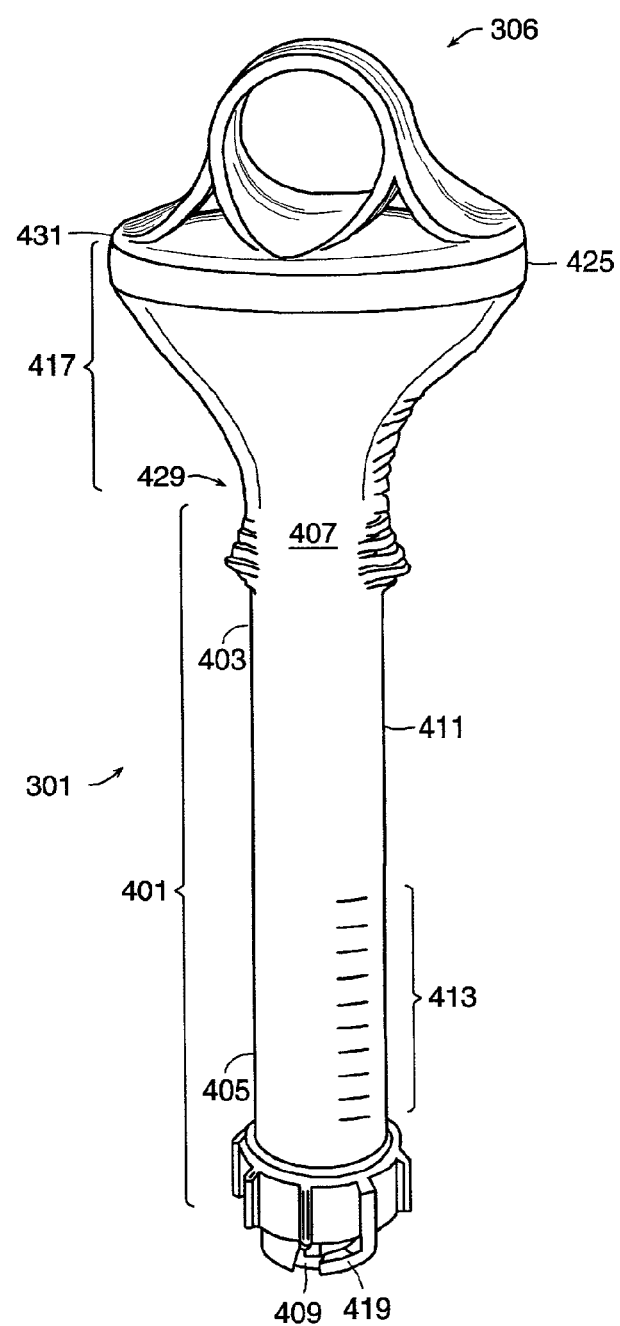
Figure 17:
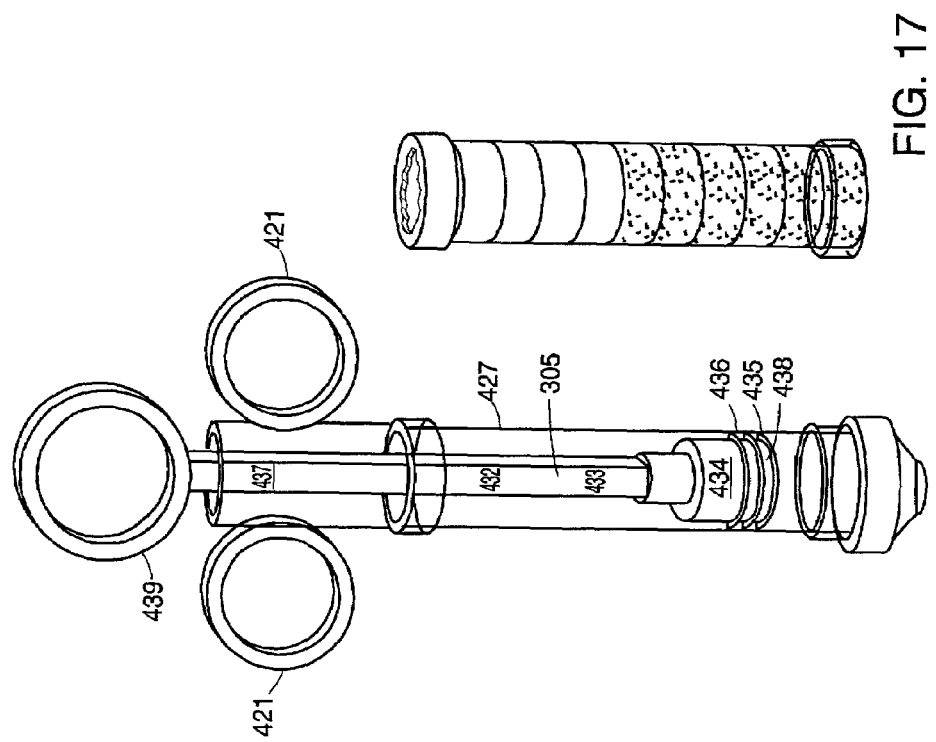

Now referring to FIG. 16, fluid retention chamber 301 receives and holds the precursor fluids delivered from the manifold, and contains the gel formed by the mixed precursor fluids. It preferably has a tube portion 401 comprising upper and lower end portions 403 and 405 forming upper and lower openings 407 and 409,respectively. It may also hold the bone material (allograft, autograft or DBM) included in the graft. The outer wall 411 of the chamber may be translucent and include volume gradations 413 which allow for accurate visualization of the contents placed therein. Preferably, the tube portion is cylindrical. In some embodiments, the volume of the tube portion is between 10 and 20 cc, more preferably about 15 cc. The tube portion may also include ribs 415 disposed upon the upper end portion of the outer wall for ease in gripping the chamber. The rib design includes a plurality of successive ribs rising farther off the chamber wall as the ribs proceed towards the lower end of the chamber. Alternatively, the upper end portion of the outer wall may form a pair of rings, 421, as shown in FIG. 17.

For the purposes of the present invention, a "fluid retention chamber" has a shape configured to retain the precursor fluids while they mix and gel, and preferably to allow the easy removal the gel therefrom in a substantially intact form. Preferably, it has an inner diameter of at least 10 mm (more preferably at least 15 mm) to allow easy removal of the gel. In some embodiments, the inner diameter is between 10 mm and 20 mm. Also, preferably, it has a volume of at least 1 cc, more preferably at least 3 cc, more preferably at least 5 cc, most preferably at least 10 cc so that it may retain large amounts of the mixed liquids.

In some embodiments, the manifold of the present invention is manufactured by injection molding upper and lower manifold halves, each having exposed half-tube shapes, and then welding the halves together, thereby forming the intra-manifold tubing. In another embodiment, the upper and lower manifold halves are injection molded, discrete intra-manifold tubing is then attached to the respective openings, and then the halves are attached. In the second embodiment, the manifold halves act as a protective housing for the tubing.

The fluid retention chamber of the present invention may optionally contain addiotnal biocompatible, implantable graft materials. Particularly suitable graft materials include, for example, isolated mineralized cancellous bone sections, powders or granules of mineralized bone, demineralized cancellous bone sections, powders or granules of demineralized bone, guanidine-HCl extracted demineralized bone matrix, sintered cortical or cancellous bone, coralline hydroxyapatite sold by Interpore under the trade name Interpore 500, or Interpore 200, and granular ceramics such as that incorporated into the bone graft substitute Collagraft sold by Zimmer, or filamentous sponges. Other suitable graft materials may include ceramics comprising calcium phosphate such as, for example, hydroxyapatite or tri-calcium phosphate; as well as demineralized bone matrix; or mineralized bone matrix. Other suitable graft materials include biopolymers such as, for example, polylactic acid, polyglycolic acid, polygalactic acid, polycaprolactone, polyethylene oxide, polypropylene oxide, polysulfone, polyethylene, and polypropylene. Other suitable graft materials are hyaluronic acid, which may be purified with or without crosslinking, bioglass, gelatin and collagen.

In some embodiments, the graft chamber may further comprise a funnel 417 located at the upper end of the chamber. The funnels helps deliver graft material into the tube portion 401. The funnel also provides additional mixing volume for insuring complete mixing of the graft material. The volume of the funnel may be between 30 and 60 cc, preferably about 45 cc. Preferably, the funnel is translucent. Although the funnel is preferably formed continuously with the tube portion, it may also be removable.

Therefore, in accordance with the present invention, there is provided a graft delivery chamber comprising:
   a) a tube portion 401 comprising upper and lower ends 403 and 405 forming upper and lower openings 407 and 409, respectively, the tube portion having a sterile inner wall 427, and
   b) a funnel portion 417 having:
      i) a lower end 429 attached to the upper end 403 of the tube portion, the lower end 429 having a first diameter, and
      ii) an upper end 431 having a second diameter, wherein the first diameter is smaller than the second diameter.

The lower end 405 of the chamber may be shaped to interlock with the upper end of the manifold connector. For example, the lower end of the chamber may have external threads 419 on its outer wall 411 for locking reception with internal threads formed on a manifold connector. Alternatively, the threads may be replaced with corresponding locking tabs.

Preferably, the funnel portion is integral with the tube portion, as shown in FIG. 16. Preferably, the upper end of the tube portion comprises a plurality of ribs 415 (preferably the height of the ribs increasing in height as the ribs proceed from the upper to lower end of the tube portion.

In embodiments in which the chamber is prefilled with graft materials such as bone particles, upper and lower ends have a peelable film 423 (as shown in FIG. 17B) attached thereto to assure the sterility of the bone particles therein.

Once filled with graft materials such as bone particles, it is often desirable to shake the chamber in order to assure a homogeneous and uniform distribution of the bone particles prior to fluid introduction. Preferably, the chamber further comprises a lid 306 having a diameter corresponding to the second diameter of the funnel. Preferably, the lid comprises a lip extending from the circumference of the lid. Now referring to FIG. 18, funnel lid 306 helps retain the bone particles within the chamber during the shaking procedure. Optionally, the lid may have a lip 425 which allows it to tightly snap onto the upper end of the funnel and secure attachment thereto.

Now referring to FIG. 17, plunger 305 holds the graft materials such as bone particles in place while the chamber is filling with the precursor fluids so that the particles do not overflow the chamber. The plunger may also be used to push out the gelled log from the chamber after the precursor-bone mixture has been gelled. The lower end 433 of the plunger may form a tip 434 whose radius 436 is sized to provide a circumferential seal with the inner wall 427 of the chamber. The tip may have a porosity selected to allow air to pass through the tip, thereby providing venting and easing the entry of the precursor fluids into the chamber. Preferably, the tip has at least one radial transverse groove 435 which helps form a transverse passage 438 between the groove and the chamber inner wall. This passage allows fluid to flow around the tip and up the inner wall, thereby providing the user with a convenient visual indication that sufficient fluid has been introduced into the chamber. In some embodiments, the groove is helical. The upper end 437 of the plunger may form a ring 439 for ease of handling. Preferably, the plunger has an integral design.

Therefore, in accordance with the present invention, there is provided a graft delivery chamber having an inner wall, comprising:

a) a tube portion 401 comprising upper and lower ends 403 and 405 forming upper and lower openings 407 and 409 respectively, the tube having a sterile inner wall 427, and b) a plunger comprising i) a rod 432 having a lower end 433, and ii) a tip 434 attached to the lower end of the rod, the tip having a radius sized to provide a circumferential seal with the inner wall 427 of the chamber, wherein the tip has at least one radial transverse groove 435 to form a transverse pore between the groove and the chamber inner wall. Preferably, the groove is helical.

Figure 18A:
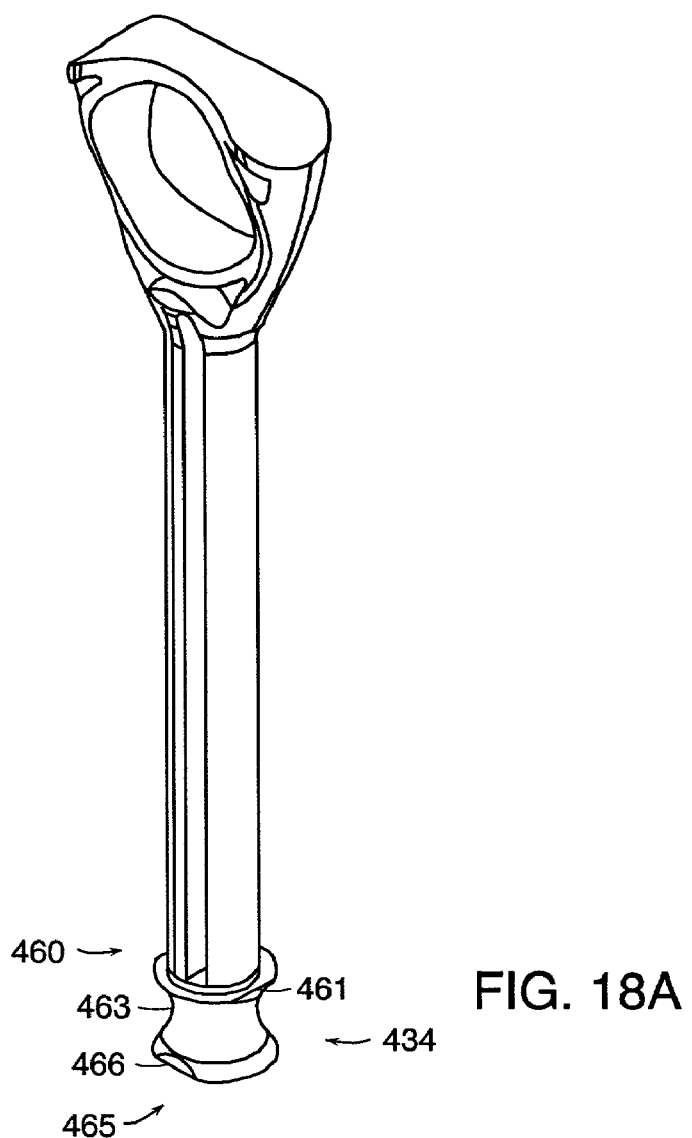
Figure 18B:
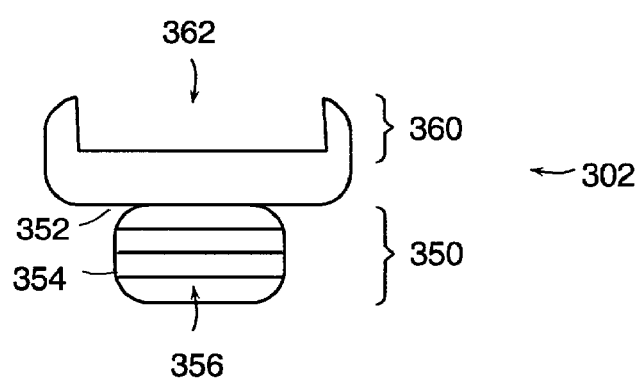

In some embodiments, as shown in FIG. 18, the tip comprises i) an upper disc 460 forming an upper flat 461, a recessed portion 463, and ii) a lower disc 465 forming a lower flat 466. The upper and lower openings form the extremities of the transverse pore groove discussed above. Since, these particular openings are located at different radial positions along the tube inner wall, a fully radial seal by the tip radii is assured. Alternatively, the flats may be replaced by transverse through holes.

When the plunger of FIG. 18*a* is used, the recessed portion 463 forms a dead volume between the upper and lower radii of the tip. This dead volume is a useful feature in that it acts as a sink for excess precursor fluid which has overflown the intended reaction space. By trapping the excess fluids in this manner, the dead volume minimizes the chances that the precursor fluids will exit the entire fluid retention chamber.

Now referring to FIG. 15, end caps 302 may be used to simply retain the graft materials such as bone particles within the chamber when the chamber is shaken. They are shaped to occlude at least one opening of the chamber. In some embodiments, the end cap has a protrusion 441 shaped for reception in the inner wall 427 of the chamber tube 301. In other embodiments, the end cap has a recess 443 shaped for receiving the outer wall 428 of the tube. In some embodiments, as in FIG. 15, the end cap has a shape so as to both be receivable in the inner wall of the chamber tube and capable of receiving the outer wall of the tube, thereby allowing occlusion of either end of the tube.

Therefore, in accordance with the present invention, there is provided a graft delivery chamber comprising:

a) a tube portion 401 comprising upper and lower ends 403 and 405 forming upper and lower openings 407 and 409 respectively, the tube having a sterile inner wall, and b) an end cap shaped to occlude at least one opening of the chamber, wherein the end cap is attached to an end of the tube portion In one preferred embodiment, the cap 302 comprises a cylinder portion 350 having a first and second end 352,354, and shaped to fit inside the tube portion of the fluid retention chamber, and a disc portion 360 attached to the first end 352 of the cylinder and having a recess 362 shaped to receive the outer wall of the fluid retention chamber. Preferably, the cylinder portion of the end cap is threaded 356 and the lower end of the inside wall of the tube portion of the receiving chamber has a corresponding thread (not shown) so that the end cap can be screwed onto the receiving chamber.

Manifold 309 of FIG. 20 may additionally include stand portions 550 shaped for receiving the lower end of the graft chamber while the chamber is being filling with graft materials such as bone particles. In one embodiment, the stand portion comprises a recess 562 in the upper surface 92 of the base shaped to receive the lower end of the tube portion of the chamber and the cap fitted thereto. Alternatively, the stand portion may be provided as a stand alone component, as in FIG. 15.

Therefore, in accordance with the present invention, there is provided a manifold for providing fluid to a graft delivery tube, comprising:

a) an output port having at least one opening, b) first and second input ports, each input port having at least one opening, c) first and second tubes, each tube having a sterile inner surface and first and second ends, the first end of the first tube being in fluid communication with the opening of the first input port, the first end of the second tube being in fluid communication with the opening of the second input port, the second end of each tube being in fluid communication with at least one opening of the output port, d) a base having an upper surface, wherein the output port is located on the upper surface of the base, and e) a graft stand shaped upon the upper surface of the base to attach to a fluid retention chamber.

Figure 19A:
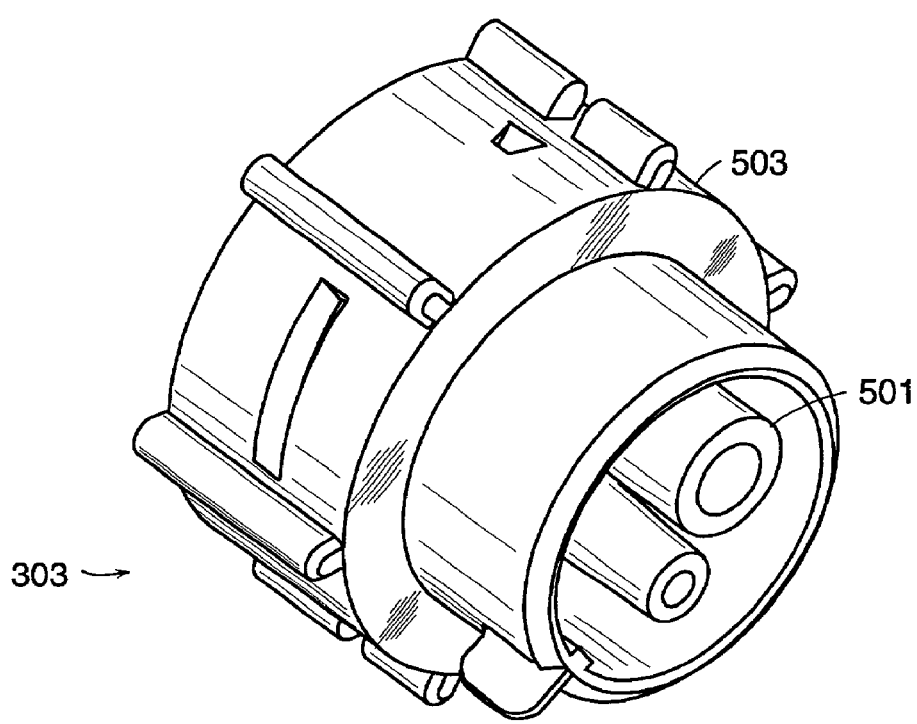

Now referring to FIG. 19*a*, manifold connector 303 comprises a port portion 501 shaped to be received in the manifold and a collar portion 503 shaped for receiving the outer wall of the fluid retention chamber. This connector serves to retain the graft materials such as bone particles during shaking and also to fluidly connect the chamber to the output port of the manifold during fluid introduction. The connector has a valve means which prevents flow therethrough during shaking, but allows flow therethrough during fluid introduction. In one embodiment, both the port and collar portions have an opening sized to permit flow of the precursor fluids therethrough. During shaking, these openings are oriented so that they do not line up, thereby preventing flow from one end of the connector to the other. During fluid introduction, the openings are aligned and allow fluid flow.

Figure 19B:
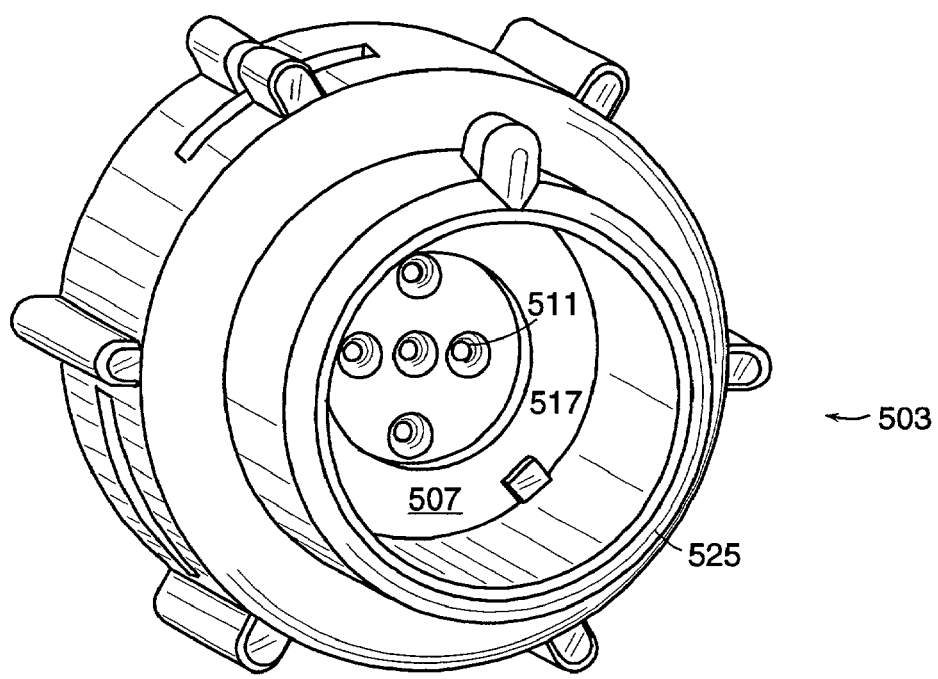
Figure 19C:
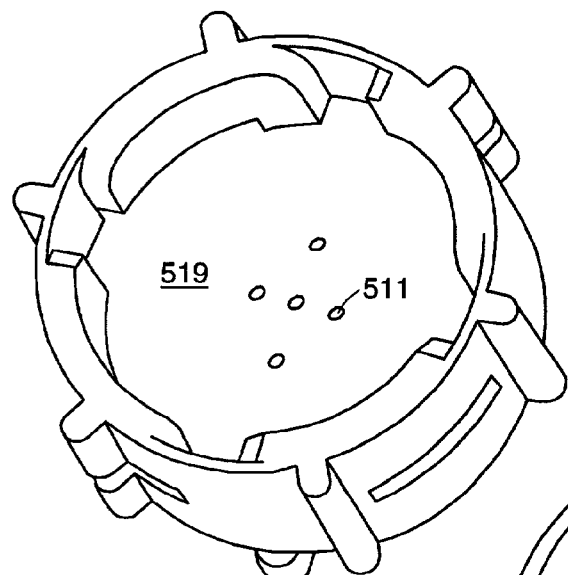
Figure 19D:
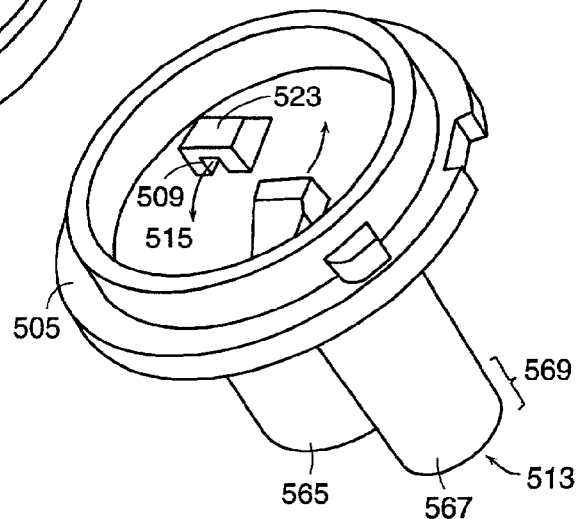

Collar portion 503 of the manifold connector is shown alone is FIG. 19*b* (lower view) and FIG. 19*c* (upper view), while port portion 501 is shown alone is FIG. 19*d*. The manifold connector presented by FIGS. 19*b*–19*d* have a mixing chamber and no valve, while the manifold connector presented by FIG. 19*e* has a valve and no mixing chamber.

Figure 19E:
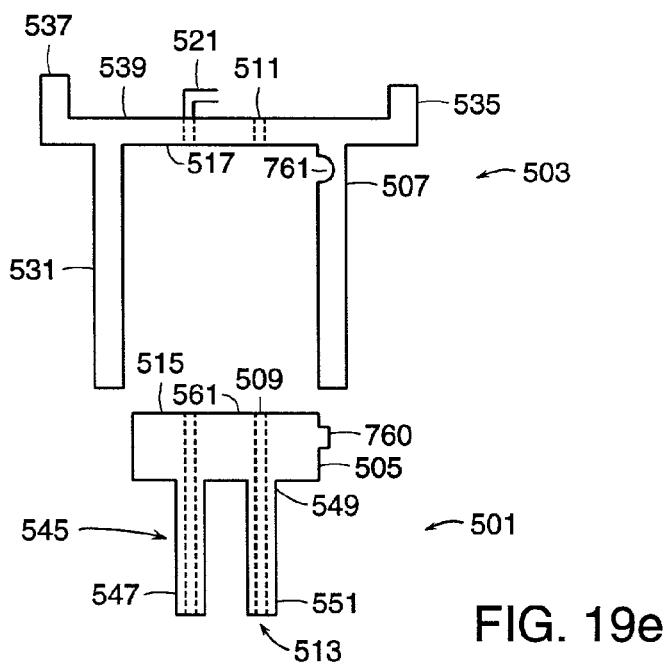

Now referring to FIG. 19*e*, upper end 505 of port portion 501 is shaped to be rotatably received with lower end 507 of collar portion. Port portion 501 rotates radially relative to the lower end of collar portion 507 in order to open and close the valve formed by opening 509 and fluid apertures 511. Therefore, the valve may be conveniently closed when shaking is desired and open when the port portion is locked onto the manifold. During fluid flow, fluid flows from delivery syringes into port entry portion 513 and exits through openings 509. Preferably, the upper surface of port portion 515 bears against the lower surface 517 of collar portion 503 so that openings 509 in the port portion bear against openings 511 in the collar portion 503. In those embodiments, the upper surface 519 of the collar portion 503 may form hoods 521 which direct the fluid flowing from openings 511 in a lateral direction.

However, in some embodiments (FIGS. 19b–d), there may be a space between the respective port and collar openings to provide a mixing space for the fluids. If a mixing chamber is provided, the upper surface of the port portion 515 may form hoods which direct the fluid flowing from openings 509 in a lateral direction. This improves mixing.

Therefore, in accordance with the present invention, there is provided a connector for connecting a fluid retention chamber and a fluid delivery manifold, the connector comprising:
a) a collar portion 503 having:
  i) a lower end portion 507 having an outer surface 531 shaped for attachment to an output port of the manifold, and an inner surface 517, and
  ii) an upper end portion 535 having an outer surface 537 shaped for attachment to the fluid retention chamber, and an inner surface 539, and
  wherein the inner surface 517 of the lower end portion 507 and the inner surface 539 of the upper end portion 535 define a having thickness T, the thickness having at least one transverse hole 511 therethrough, and
b) a port portion 501 having:
  i) a lower end portion 545 being sterile and comprising at least one tube 547 having an upper end 549 and a lower end 551, the lower end 551 shaped for attachment to an output port 553 in the manifold 555 and for fluid connection with an output opening 557, and
  ii) an upper end portion 505 shaped for reception within the lower end 507 of the collar portion 503 and comprising an upper surface 561 having opening 509 in fluid connection with the upper end 549 of the tube 547 of the lower end portion 545, wherein the upper end portion 505 of the port portion 501 is received within the lower end portion 507 of the collar portion 503.

In one embodiment, the upper surface 561 of the upper end portion 559 of the port portion 501 forms at least one hood 563 about its at least one openings. In another embodiment, the upper surface 561 of the upper end portion 559 of the port portion 501 bears against the inner surface 533 of the lower end portion 507 of the collar portion 503.

Preferably, the connector further comprises a valve means for providing fluid communication between the transverse hole 511 of the collar portion 503 and the opening 563 of the port portion 501. This valve means allows graft material such as bone particles to be retained in the receiving chamber during mixing (when closed) and fluid precursors to enter the receiving chamber (when open). In one preferred embodiment, the upper end portion 559 of the port portion 501 is shaped to be radially rotatable within the lower end portion 507 of the collar portion 503 between two positions by a tongue 760 and groove 761 mechanism. Preferably, this selected shape allows radial rotation of the upper end portion to a first position wherein the transverse holes 511 of the collar portion 503 and the opening 563 of the port portion 501 are in fluid connection, and to a second position wherein the transverse holes 551 of the collar portion 503 and the opening 509 of the port portion 501 are in fluid isolation. In another preferred embodiment, a conventional valve is located between the transverse hole 511 of the collar portion 503 and the opening 563 of the port portion 501.

In some embodiments, the manifold connector may comprise an upper surface having an opening therethrough for providing fluid communication between the a fluid retention chamber and a fluid delivery manifold, wherein a hood is formed around the opening. Preferably, the hood extends from the upper surface at an angle of less than 90 degrees and produces an opening which faces the upper surface of the manifold connector, as shown in FIG. 19.

Although the system provided in FIG. 20 produces suitable graft, it nonetheless has some drawbacks. For example, the exit port 560 of manifold 309 must be configured to accept not only the mating surface 525 of the collar portion of the manifold connector, but the mating surface 569 of the port portion of the connector as well. Since the mating surface of the port portion includes a pair of independent tubes 565 and 567, the exit port 650 of the manifold must be configured with two recesses 573, 575 to receive each tube 565, 567. As shown in FIG. 20, this requirement necessitates a complex port design in the manifold. In addition, this design may make it difficult to meet performance specifications when the components are injection molded.

Figure 22:
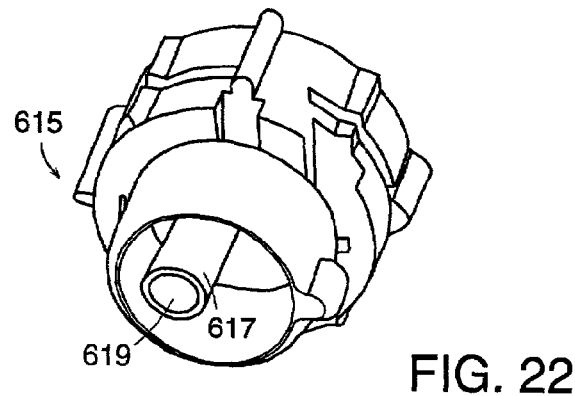
Figure 21:
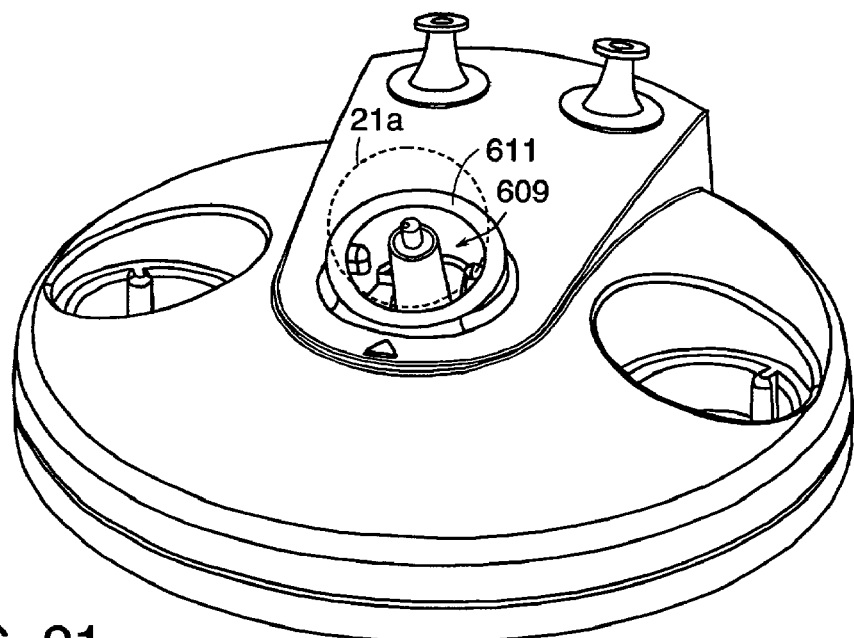
Figure 21A:
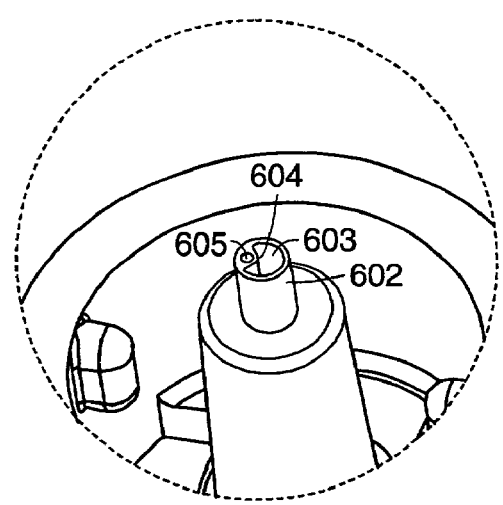

Therefore, in one embodiment of the present invention, the exit portion of the manifold tubing has a dual lumen design, as shown in FIG. 21. In particular, dual lumen tube portion 601 comprises exit openings 603,605 having a shared surface 604 with a single outer tube 602. Dual lumen tube portion 601 provides the advantage of maintaining the distinct delivery of the fluids into the manifold, but requires only a single recess 609 in the manifold exit port 611 in order to attach to a fluid retention chamber. Similarly, and now referring to FIG. 22, in the corresponding manifold connector 615, the port portion 617 need have only a single opening 619 to accommodate the dual lumen tube. Thus, only a single physical connection between need be made to make two fluid connections.

Therefore, in accordance with the present invention, in preferred embodiments, the exit portions of each manifold tube are provided as a single, dual lumen tube portion.

Preferably, in some embodiments, the port tube is off-center, thereby allowing the valve mechanism described in the dual cap design to be used.

Figure 23A:
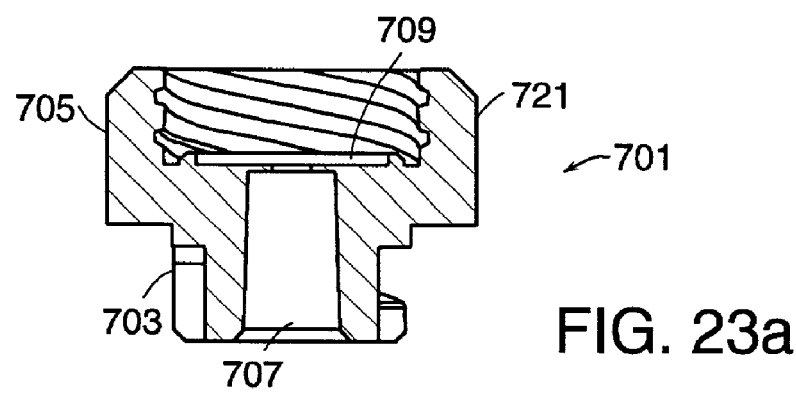
Figure 23B:
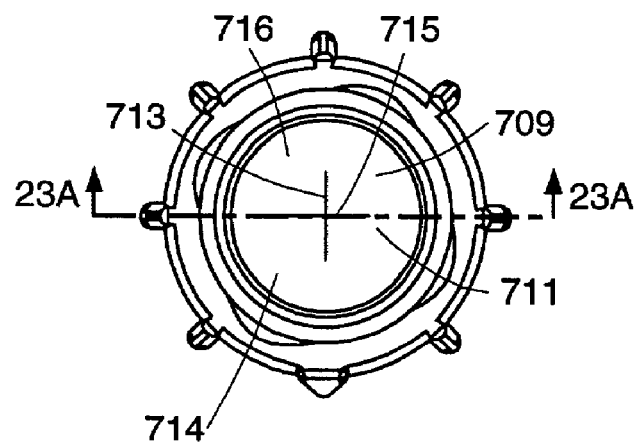
Figure 23C:
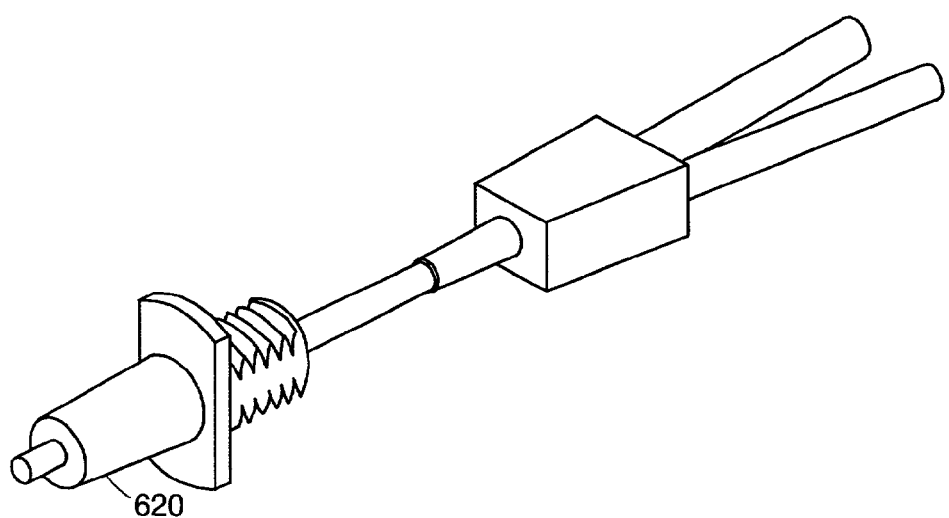

However, even with the dual lumen tube design, the two-piece design of the manifold connector may present potential failure modes. Therefore, now referring to FIG. 23a, there is provided a single piece manifold connector 701. This single-piece manifold connector comprises a lower end 703 shaped to attach to the exit port of the manifold and an upper end 705 shaped to attach to the fluid retention chamber. Preferably, the single-piece manifold connector comprises a lower end 703 shaped to be received in the exit port of the manifold and an upper end 705 shaped to receive the graft chamber. A recess 707 is formed on the lower end 703 of the connector 701 for recpetion of the exit port of the manifold. Now referring to FIG. 23b, upper surface 709 of the connector comprises at least one slit 711 producing flaps 714 and 716. Preferably, upper surface 709 of the connector comprises at least a pair of slits 711 and 713 whose intersection 715 produces four flaps. When the lower end 703 of this manifold connector is attached to a manifold exit port having a dual lumen design, the upper end 602 of the dual lumen tube 601 protrudes through the slits 711 formed on the upper surface, thereby providing fluid connection between the manifold and the graft chamber. This design is advantageous because it provides the needed fluid communication and eliminates the problems associated with a two-piece design.

Therefore, in accordance with the present invention, there is provided a connector for connecting a fluid retention chamber and a fluid delivery manifold, the connector comprising:
a) an upper end 705 shaped for attachment to the graft delivery chamber (the upper surface preferably having an outer annulus 721 shaped for reception of the fluid retention chamber), the upper end 705 being sterile and comprising an inner surface 709 comprising a breachable skin for extension of a tube therethrough (preferably comprising at least one slit 711 producing flaps 714 and 716), and b) a lower end 703, the lower surface being sterile and shaped for attachment to an exit port of a manifold (preferably having a recess shaped for reception of a tube) and exposing the breachable skin.

Preferably, the the breachable skin comprises at least two intersecting slits producing four flaps. In some embodiments, and now referring to FIG. 23b, a collar 620 (preferably having a tapered outer surface) is fitted over the end of the dual lumen tube in order to provide the rigidity and support necessary for breaching the inner surface 709 of the manifold connector. It also provides a fluid tight seal with the inner surface 709 of the manifold connector.

Figure 24A:
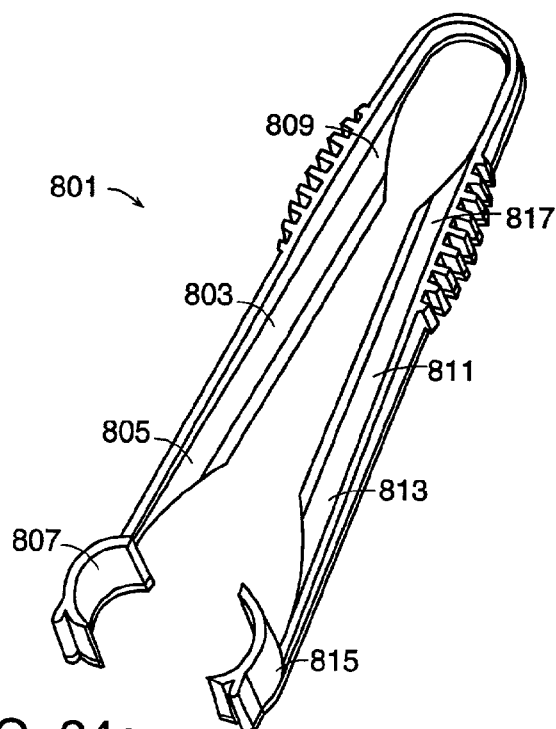
Figure 24B:
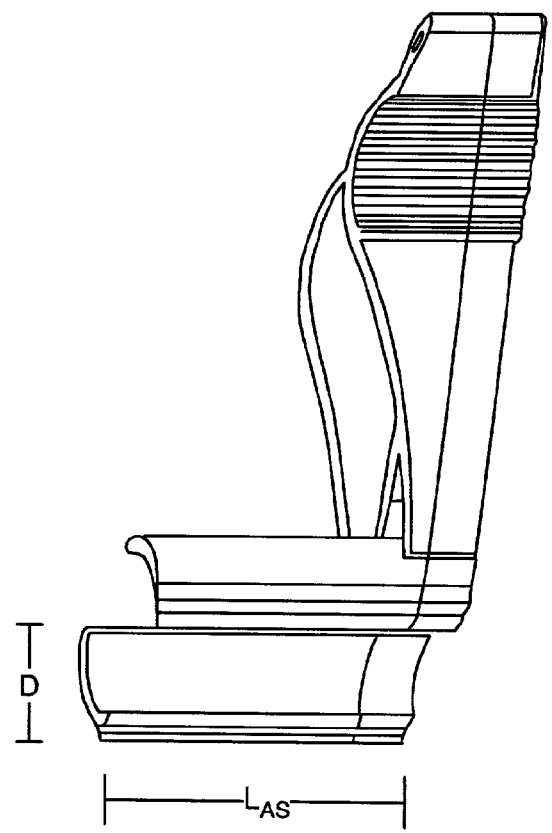
Figure 27:
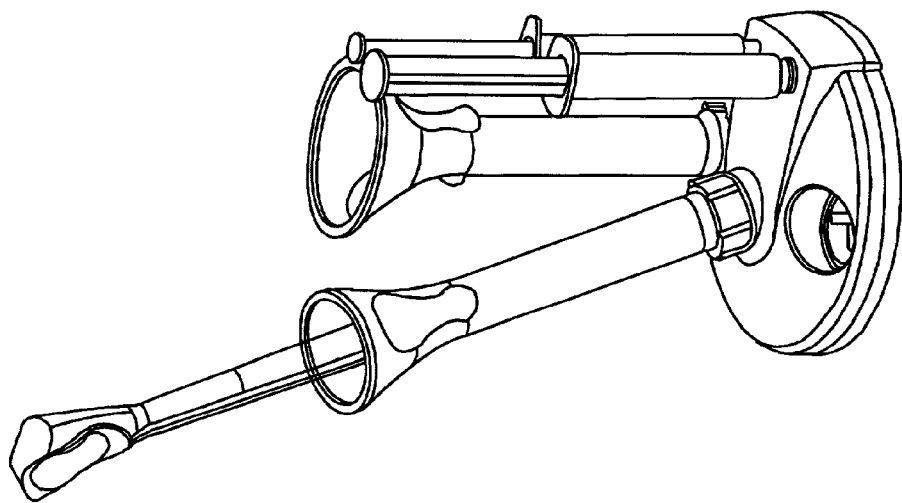
Figure 26:
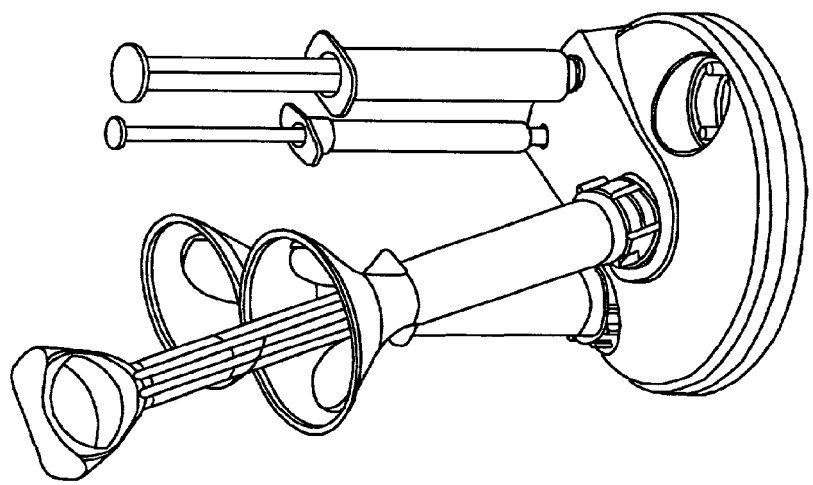

Now referring to FIG. 24a, graft forceps 801 have semi-cylindrical ends 807 and 815 shaped to suitably grasp and place the cylindrical-shaped gelled logs produced by the chamber. Preferably, end portions 807 and 815 are shaped to correspond with the shape of the gelled graft produced within the chamber. As shown in FIG. 24b, the length $L_{AS}$ of the arcuate shape is relatively long in order to accomodate the cylindrical geometry of the gelled log.

Therefore, in accordance with the present invention, there is provided graft forceps 801 suitable for handling gelled graft, comprising:

a) a first tyne 803 having i) a lower end 805 forming a first arcuate shape 807 having a sterile inner surface 821, and ii) an upper end 809, and b) a second tyne 811 having a lower end 813 forming a second arcuate shape 815 having a sterile inner surface 823, and ii) and an upper end 817, wherein the upper ends 809, 817 are connected, wherein each arcuate length has a length $L_{AS}$ and a diameter D, and wherein the length $L_{AS}$ of each arcuate shape is at least two times (and preferably at least three times) its diameter D.

The apparatus of the present invention can be made from any conventional biomaterial, including plastics such as polymers and metals. However, in some embodiments, the apparatus is designed as a disposable and so an inexpensive plastic such as polycarbonate is used. Preferably, the components of the present invention are sterile.

EXAMPLE I

In some cases, the surgeon may choose to use autograft (i.e., bone from the patient) as a source of matrix cells and bone growth factor to complement the growth factors in the platelets in the PRP precursor and accelerate the bone growth process. Therefore, in one preferred embodiment, and now referring to FIG. 25, the graft chamber 412 having an attached funnel 307 is placed on a stand 304 (step 1), and the barrel of the chamber is filled with graft materials such as bone particles through the funnel 307 (step 2). The bone graft may be optionally tamped, if desired. Next, lid 306 is placed on the funnel 307 (step 3), and the chamber syringe is inverted and shaken in order to homogeneously distribute the bone particles (step 4). The syringe is then re-inserted into the stand (step 5), the lid is removed, and the bone graft is tamped into the syringe (step 6). At this point, the funnel is removed (step 7), and the syringe is removed from the stand (step 8). Next, the end cap capping the first opening of the syringe is replaced with a manifold connector 303 (step 8), the syringe is fitted into the receiving port of the manifold connector (step 9).

Once all three syringes are received in their respective ports, plungers of the delivery syringes are simultaneously depressed (step 10), thereby forcing the precursor fluids through the manifold and into the receiving syringe, wherein the precursor fluids mix and form a clotted fibrin gel within the receiving syringe. After a period of time suitable to insure adequate gelling of the precursor fluids, a plunger is inserted in the back of the receiving syringe (step 11), and the receiving syringe is removed from the manifold (steps 12–13).

Next, the manifold connector is removed and the plunger is depressed to force the clotted gel/bone graft mixture out of the receiving syringe (steps 14–15).

EXAMPLE II

In some cases, the surgeon may choose to use allograft (i.e., bone from another human source) as a source of bone, matrix and growth factors in addition to autograft from the patient. In this example, the syringe is prefilled with bone graft (allograft), and so initially has end caps. The prefilled syringe is placed upon stand and the upper end cap is replaced with a funnel. The remaining steps, beginning with step 3, of example I are followed.

EXAMPLE III

In some cases, the surgeon may choose to simply use allograft (bone from another human source). In this embodiment, the syringe is prefilled with bone graft (allograft), and so initially has two end caps. An end cap is replaced with a manifold connector, and the prefilled syringe is then placed in a stand. Once the second end cap is removed, and the delivery syringes are also placed in the manifold, the remaining steps of example I are followed.

EXAMPLE IV

In one preferred method of using the present invention, the following procedure is followed:

1. Open outer package and deliver sterile inner package onto a sterile field.
2. Open inner package.
3. Remove manifold and place onto sterile field.
4. Remove graft chamber and remove lid from graft chamber. Do not remove end cap from chamber.
5. Place cap end of graft chamber into one of the chamber stands in the manifold.
6. Fill graft chamber with the desired amount of bone graft material(s). The cylindrical portion of the graft chamber is approximately 15 cc. If desired, the lid can be placed back onto the graft chamber to mix the contents by manual agitation of the graft chamber.
7. With the chamber in the stand and lid removed, place the plunger tip onto the column of graft material by sliding it into the top of the graft chamber. If necessary, the plunger can be used to compress the material into the chamber to remove as much air as practical.
8. Remove the graft chamber from stand and insert into port in center of manifold by aligning arrow on end cap with arrow on manifold and turning clockwise.

9. To fill graft chamber with fluid(s), attach syringe(s) containing source fluid(s) to luer lock connection(s) on manifold and depress plunger(s). Fill until fluid is seen around the tip of the plunger in the graft chamber.
10. Remove graft chamber from manifold by turning end cap counter clockwise in manifold. To delivery the graft material, remove end cap.
11. Using the plunger, gently expel graft chamber contents into the desired graft location.

EXAMPLE V

In some embodiments, the mixed fluids retained in the fluid retention chamber may be directly injected into the body. In such a case, an opening in the fluid retention chamber may be fitted with a needle, and a plunger may be used to push the mixed fluids from the fluid retention chamber through the needle and into the patient.

EXAMPLE VI

In some conventional spinal surgeries, a pair of intervertebral cages are used. Therefore, in some embodiments of the present invention, the apparatus may comprises two fluid retention chambers and the manifold may comprise two output ports. This apparatus allows the simultaneous dosing of the pair of cages to be used in the surgery, thereby saving time. In one embodiment, a first intramanifold tube extends from a single input port and then branches off into two portions to provide delivery of the precursor fluid to each output port, thereby feeding each output port with a single input port.

EXAMPLE VII

Although the benefits of the present invention have been discussed in light of using the manifold to deliver two fluids into a fluid retention chamber, the manifold may also be used in a reverse manner. That is, in some embodiments, the manifold may be used to draw fluids from the fluid retention chamber into the two delivery syringes mounted to the input ports. In one embodiment, a fluid retained in the fluid retention chamber may flow into the manifold through an output port in the manifold, flow through the tubing and enter the delivery syringes. In some embodiments, this may be accomplished by withdrawing the depressed pistons housed within the delivery syringes mounted to the input ports of the manifold. In some embodiments, therefore, two fluids are initially held in the delivery syringes, the pistons in those syringes are depressed, thereby flowing the fluids through the manifold and into the fluid retention chamber, thereby causing their mixing. Then, the depressed pistons are raised, with the resulting vacuum causing flow of the mixed fluids back into the delivery syringes. In some embodiments, the delivery syringes are then fitted with needles, and the mixed fluids may then be injected into a patient or other site through the needle.

The present invention is useful not only in spinal fusion surgeries, but also other surgeries requiring the delivery of any material desirable for enhancing the repair of bone, cartilage or tendon, including graft materials therefor. These typically include spinal surgeries such as posterior lumbar fusion, interbody fusion and illiac crest backfill; orthopaedic applications such as joint revisions, humeral fractures, wrist and ankle arthrodesis; porous coating pre-coats; oral maxillofacial applications such as reconstruction; cranial bore application; and trauma surgeries such as general fusion augmentation and bone void filling.

Although the benefits of the present invention have been discussed in light of its application to a PRP-thrombin system for producing a gel, the apparatus and manifold of the present invention can also be used for the mixing and retention of other biological fluids. Such fluids include bone marrow aspirate, autologous blood, and other-plasma based materials. The fluids may include peripheral blood, NaCl, saline, and suitable buffers. The fluids may be used with or without additional therapeutic agents. Coagulation agents other than thrombin may also be used.

Likewise, although the benefits of the present invention have been discussed in light of its bone graft application, the apparatus and manifold of the present invention can also be used for the mixing and retention of other biological fluids desired for use in other graft applications as well, such as cartilage and tendon grafts.

We claim:

1. An apparatus comprising a fluid retention chamber having an opening, and a manifold comprising:
   a) an output port adapted for attachment to a fluid retention chamber, the port having at least one opening,
   b) first and second input ports, each port adapted for attachment to a delivery syringe, each input port having an opening, and
   c) first and second tubes, each tube having a sterile inner surface, and entry and exit portions,
   d) a continuous base having an upper and a lower surface, wherein each port is located upon the base and extends upward from the upper surface, and
   e) first and second delivery syringes, each syringe having a bore, a syringe opening and a plunger contained within the bore,
   wherein the syringe opening of each syringe is attached to the opening of the respective input port,
   the entry portion of the first tube being in fluid communication with the opening of the first input port, the entry portion of the second tube being in fluid communication with the opening of the second input port,
   the exit portion of each tube being in fluid communication with the at least one opening of the output port,
   wherein each port opening has a centerpoint at the upper surface of the base, wherein the three centerpoints define a triangle.

2. The apparatus of claim 1 wherein the triangle defines an angle α of between 5 and 90 degrees.

3. The apparatus of claim 2 wherein the angle α is between 5 and 45 degrees.

4. The apparatus of claim 2 wherein the angle α is between 10 and 30 degrees.

5. The apparatus of claim 1 wherein the plunger of each delivery syringe extends upward from the upper surface of the base.

6. The apparatus of claim 1 wherein the first delivery syringe contains a first fluid comprising PRP, and the second delivery syringe contains a first fluid comprising thrombin.

* * * * *